United States Patent
Neubardt

(10) Patent No.: US 11,992,419 B2
(45) Date of Patent: May 28, 2024

(54) SIDE POCKET SPINAL FUSION CAGE

(71) Applicant: Seth Neubardt, Rye, NY (US)

(72) Inventor: Seth Neubardt, Rye, NY (US)

( * ) Notice: Subject to any disclaimer, the term of this patent is extended or adjusted under 35 U.S.C. 154(b) by 0 days.

(21) Appl. No.: 18/051,673

(22) Filed: Nov. 1, 2022

(65) Prior Publication Data

US 2023/0112129 A1 Apr. 13, 2023

Related U.S. Application Data

(63) Continuation of application No. 17/101,746, filed on Nov. 23, 2020, now Pat. No. 11,529,242, which is a continuation of application No. 16/219,202, filed on Dec. 13, 2018, now Pat. No. 10,893,953.

(60) Provisional application No. 62/623,067, filed on Jan. 29, 2018.

(51) Int. Cl.
*A61F 2/44* (2006.01)

(52) U.S. Cl.
CPC .......... *A61F 2/4465* (2013.01); *A61F 2/4455* (2013.01)

(58) Field of Classification Search
CPC .......... A61F 2/44; A61F 2/4455; A61F 2/446; A61F 2/4465; A61F 2/447
See application file for complete search history.

(56) References Cited

U.S. PATENT DOCUMENTS

| | | | |
|---|---|---|---|
| 5,609,635 A | 3/1997 | Michelson | |
| 5,645,084 A | 7/1997 | Mckay | |
| 6,264,656 B1 | 7/2001 | Michelson | |
| 8,303,879 B2 | 11/2012 | Bertele et al. | |
| 8,343,224 B2 * | 1/2013 | Lynn | A61F 2/4611 623/17.16 |
| 8,545,568 B2 | 10/2013 | Ulrich, Jr. et al. | |
| 8,845,733 B2 | 9/2014 | O'Neil et al. | |
| 8,900,312 B2 | 12/2014 | McLean et al. | |
| 9,314,348 B2 | 4/2016 | Emstad | |
| 9,480,576 B2 * | 11/2016 | Pepper | A61F 2/4611 |
| 9,532,883 B2 * | 1/2017 | McLuen | A61F 2/28 |
| 9,668,881 B1 * | 6/2017 | Greenhalgh | A61B 90/40 |
| 10,478,313 B1 * | 11/2019 | Sweeney, III | A61F 2/4611 |
| 10,893,953 B2 * | 1/2021 | Neubardt | A61F 2/4465 |

(Continued)

OTHER PUBLICATIONS

A. L. Williams, et al., "CT Evaluation of Lumbar Interbody Fusion: Current Concepts," American Journal of Neuroradiology (Sep. 2005), vol. 26, No. 8, at pp. 2057-2066.

(Continued)

*Primary Examiner* — Eric S Gibson
(74) *Attorney, Agent, or Firm* — Knobbe, Martens, Olson & Bear, LLP

(57) ABSTRACT

A spinal implant is provided including an upper surface, a lower surface, a front surface and a back surface, two side surfaces extending between the upper surface and the lower surface, the two side surfaces extending between the front surface and the back surface and an opening positioned closer to the back surface than the front surface. The opening is provided to contain graft material that spans between a cortical rim of the upper vertebral body and the cortical rim of the lower vertebral body. The method includes packing the opening with graft material, wherein the graft material spans between the decorticated cortical rim of the upper vertebral body and the decorticated cortical rim of the lower vertebral body.

20 Claims, 32 Drawing Sheets

(56) References Cited

U.S. PATENT DOCUMENTS

| | | | |
|---|---|---|---|
| 2003/0023306 A1* | 1/2003 | Liu | A61F 2/447 623/17.11 |
| 2003/0125739 A1* | 7/2003 | Bagga | A61L 27/446 606/907 |
| 2003/0153975 A1* | 8/2003 | Byrd, III | A61F 2/447 623/17.11 |
| 2007/0208343 A1* | 9/2007 | Magerl | A61B 17/025 606/86 A |
| 2008/0154377 A1* | 6/2008 | Voellmicke | A61F 2/4611 623/17.16 |
| 2010/0256760 A1* | 10/2010 | Hansell | A61F 2/4465 623/17.11 |
| 2011/0276142 A1* | 11/2011 | Niemiec | A61F 2/4465 623/17.16 |
| 2012/0095559 A1* | 4/2012 | Woods | A61F 2/4455 623/17.11 |
| 2012/0303128 A1* | 11/2012 | Ullrich, Jr. | A61F 2/442 623/17.16 |
| 2013/0006365 A1* | 1/2013 | Pepper | A61F 2/447 606/279 |
| 2014/0058512 A1* | 2/2014 | Petersheim | A61F 2/4611 623/17.16 |
| 2014/0135930 A1 | 5/2014 | Georges | |
| 2014/0288655 A1* | 9/2014 | Parry | A61F 2/447 623/17.16 |
| 2015/0305881 A1* | 10/2015 | Bal | A61F 2/442 623/17.12 |
| 2016/0030194 A1* | 2/2016 | Ledet | A61F 2/442 623/17.16 |
| 2016/0296343 A1* | 10/2016 | Bost | A61F 2/30771 |
| 2017/0020680 A1* | 1/2017 | Cheng | A61B 17/7059 |
| 2017/0156888 A1 | 6/2017 | Neubardt | |
| 2017/0367840 A1* | 12/2017 | Martynova | A61F 2/442 |
| 2018/0078386 A1* | 3/2018 | Kieser | A61F 2/30942 |
| 2018/0200063 A1* | 7/2018 | Kahmer | A61F 2/4455 |
| 2018/0303629 A1* | 10/2018 | Lauf | A61B 17/70 |
| 2019/0231555 A1* | 8/2019 | Neubardt | A61F 2/4465 |
| 2020/0229939 A1* | 7/2020 | To | A61F 2/447 |
| 2021/0137702 A1* | 5/2021 | Neubardt | A61F 2/4455 |
| 2023/0112129 A1* | 4/2023 | Neubardt | A61F 2/4465 623/17.16 |

OTHER PUBLICATIONS

T. Sato et al., Use of Nonlinear Finite Element Analysis of Bone Density to Investigate the Biomechanical Effect in the Bone around Intervertebral Cages in Posterior Lumbar Interbody Fusion, Journal of Biomedical Science and Engineering, vol. 10, No. 10 (Oct. 2017) at pp. 445-455.

J. Rihn et al., Disc Space Preparation in Transforaminal Lumbar Fusion: A Comparison of Minimally Invasive and Open Aproaches, Clin. Orthop. Relat. Res., (Jun. 2014) at pp. 1800-1805.

* cited by examiner

SIDE POCKET SPINAL FUSION CAGE

INCORPORATION BY REFERENCE TO ANY PRIORITY APPLICATIONS

The present application is a continuation of U.S. patent application Ser. No. 17/101,746, filed Nov. 23, 2020, which is a continuation of U.S. patent application Ser. No. 16/219,202, filed Dec. 13, 2018, which claims priority under 35 U.S.C. § 119(e) to U.S. Provisional Patent Application No. 62/623,067, filed Jan. 29, 2018, the disclosures of each of these applications are hereby incorporated by reference herein in their entirety. Any and all applications for which a foreign or domestic priority claim is identified in the Application Data Sheet as filed with the present application are hereby incorporated by reference under 37 CFR 1.57.

BACKGROUND

Field

The present disclosure relates to surgical implants to promote bone fusion and surgical methods of implanting devices in the body of the patient.

Description of the Related Art

Various disorders can lead to pain and loss of mobility of the spine. Spinal fusion is a surgical technique that joins two or more vertebrae. In some methods, spinal fusion can utilize a bone graft to promote fusion between the vertebrae. Spinal fusion can also utilize an implant, often called a cage placed in the disc space between two vertebrae to be fused. The cage can be inserted from a posterior, lateral, or anterior direction depending on the nature and shape of the cage selected by the surgeon. Cages are typically made of strong plastics or metallic material, or a combination of both Spinal fusion can include fusing the two adjacent vertebrae together such that the relative motion between the two adjacent vertebrae is limited or prevented, thus reducing the pain associated with the movement of these vertebrae. Spinal fusion procedures can have many complications including infection, blood loss, nerve damage, and degeneration of adjacent vertebrae. There remains a need for improved implants and methods of spinal fusion.

SUMMARY

In some embodiments, a spinal implant is provided. The spinal implant can include an upper surface. In some embodiments, at least a portion of the upper surface is configured for placement adjacent to an upper vertebral endplate of an upper vertebral body. The spinal implant can include a lower surface, opposite the upper surface. In some embodiments, at least a portion of the lower surface is configured for placement adjacent to a lower vertebral endplate of a lower vertebral body. The spinal implant can include a front surface and a back surface. In some embodiments, the front surface is configured for insertion into a space between the upper vertebral body and the lower vertebral body. The spinal implant can include two side surfaces extending between the upper surface and the lower surface. In some embodiments, the two side surfaces extend between the front surface and the back surface. The spinal implant can include an opening positioned closer to the back surface than the front surface. In some embodiments, the opening is configured to contain graft material that spans between a cortical rim of the upper vertebral body and a cortical rim of the lower vertebral body.

In some embodiments, the spinal implant comprises only one opening. In some embodiments, the spinal implant consists essentially of one opening for containing bone graft. In some embodiments, the opening is contiguous with the back surface. In some embodiments, the opening is offset from the center of the spinal implant. In some embodiments, the front surface and at least a portion of the two side surfaces form a continuous solid body. In some embodiments, the opening comprises at least 10% of the surface area of the top surface. In some embodiments, the opening comprises at least 20% of the surface area of the top surface. In some embodiments, the opening comprises at least 10% of the length of the spinal implant. In some embodiments, the opening comprises at least 20% of the length of the spinal implant. In some embodiments, a softer, more malleable material forms at least a portion of the opening. In some embodiments, the spinal implant can include a means to secure the graft material within the opening.

In some embodiments, a method of spinal fusion is provided. The method can include providing a spinal implant. The spinal implant can include an upper surface. The spinal implant can include a lower surface. The spinal implant can include a front surface and a back surface. The spinal implant can include two side surfaces extending between the upper surface and the lower surface. In some embodiments, the two side surfaces extend between the front surface and the back surface. The spinal implant can include an opening positioned closer to the back surface than the front surface. The method can include inserting the front surface of the spinal implant into a space between an upper vertebral body and a lower vertebral body. The spinal implant can include positioning the spinal implant. In some embodiments, at least a portion of the upper surface is placed adjacent to a vertebral endplate of the upper vertebral body. In some embodiments, at least a portion of the lower surface is placed adjacent to a vertebral endplate of the lower vertebral body. In some embodiments, the opening is placed adjacent to a decorticated cortical rim of the upper vertebral body and a decorticated cortical rim of the lower vertebral body. The method can include packing the opening with graft material. In some embodiments, the graft material spans between the cortical rim of the upper vertebral body and the cortical rim of the lower vertebral body.

In some embodiments, inserting the front surface of the spinal implant further comprises an anterior approach. In some embodiments, inserting the front surface of the spinal implant further comprises a posterior approach. In some embodiments, inserting the front surface of the spinal implant further comprises a lateral approach. In some embodiments, at least a portion of an edge of the opening collapses at least one millimeter. In some embodiments, the cortical rim applies a compressive force to the graft material. In some embodiments, the upper vertebral endplate and the lower vertebral endplate remain intact. In some embodiments, cortical rim is decorticated.

BRIEF DESCRIPTION OF THE DRAWINGS

The structure and operation of the invention will be better understood with the following detailed description of embodiments of the invention, along with the accompanying illustrations, in which.

DETAILED DESCRIPTION

Figure 1:
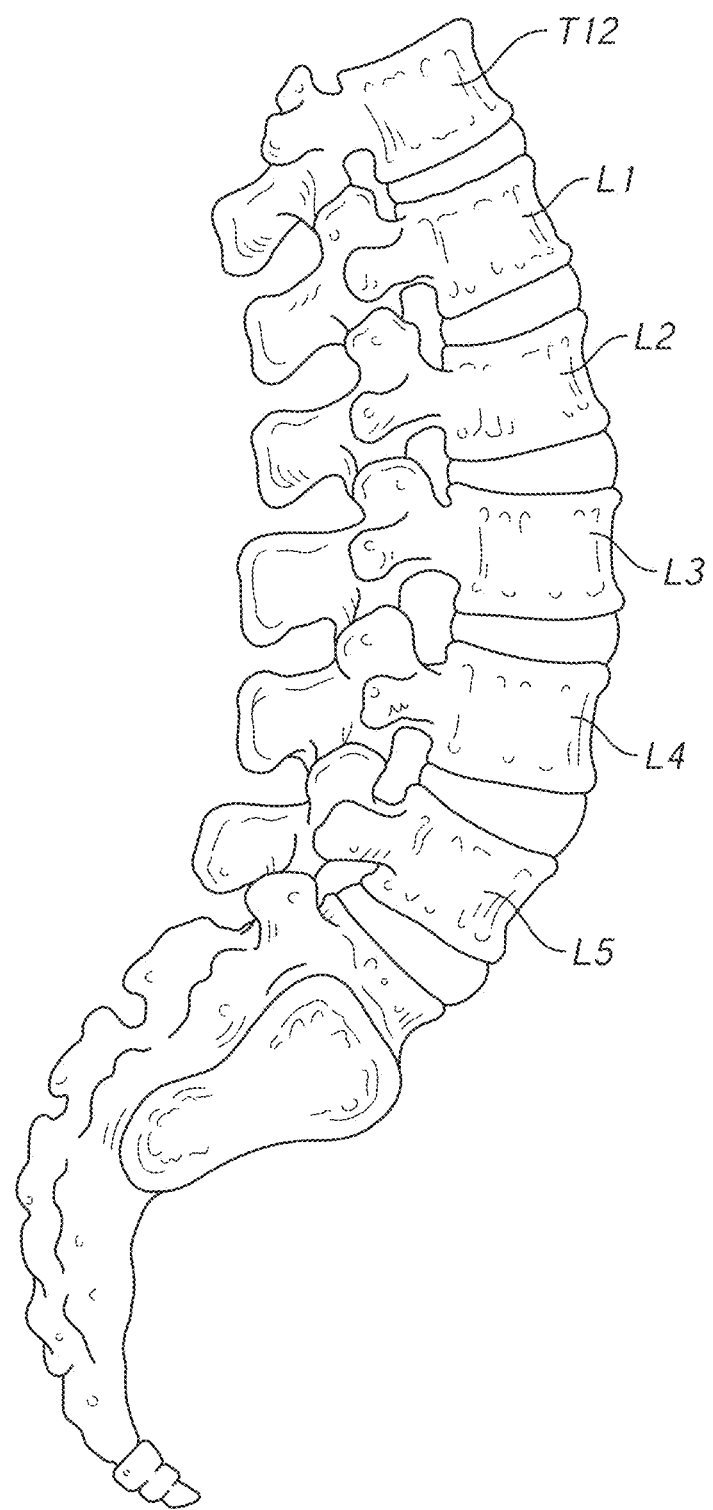
FIG. 1 is a lateral view of a vertebral column.

FIG. 1 is a lateral view of a portion of a vertebral column which includes thirty-three vertebrae. The upper twenty-four vertebrae are designed to articulate. Each vertebra is separated from adjacent vertebrae by an intervertebral disc. The lower nine vertebrae are fused in the adults with five of these vertebrae forming the sacrum and four of these vertebrae forming the coccyx. FIG. 1 illustrates the five lumbar vertebrae. There are seven cervical vertebrae (not shown), twelve thoracic vertebra (T12 shown), and five lumbar vertebrae (L1-L5 shown).

FIG. 1 illustrates how the spine has a normal curve called lumbar lordosis. The curve creates what is known as the "small of the back." Note that the edges of the vertebral bones generally define a square, but the discs in the spaces between the bones are actually wedged shaped. That is, each disc is wider at the front (anterior region) and narrower at the back (posterior region). Therefore, the distance over which any fusion of two adjacent vertebrae must occur is greater at the front or anterior region of the disc, compared to the distance at the back or posterior region of the disc.

Figure 2:
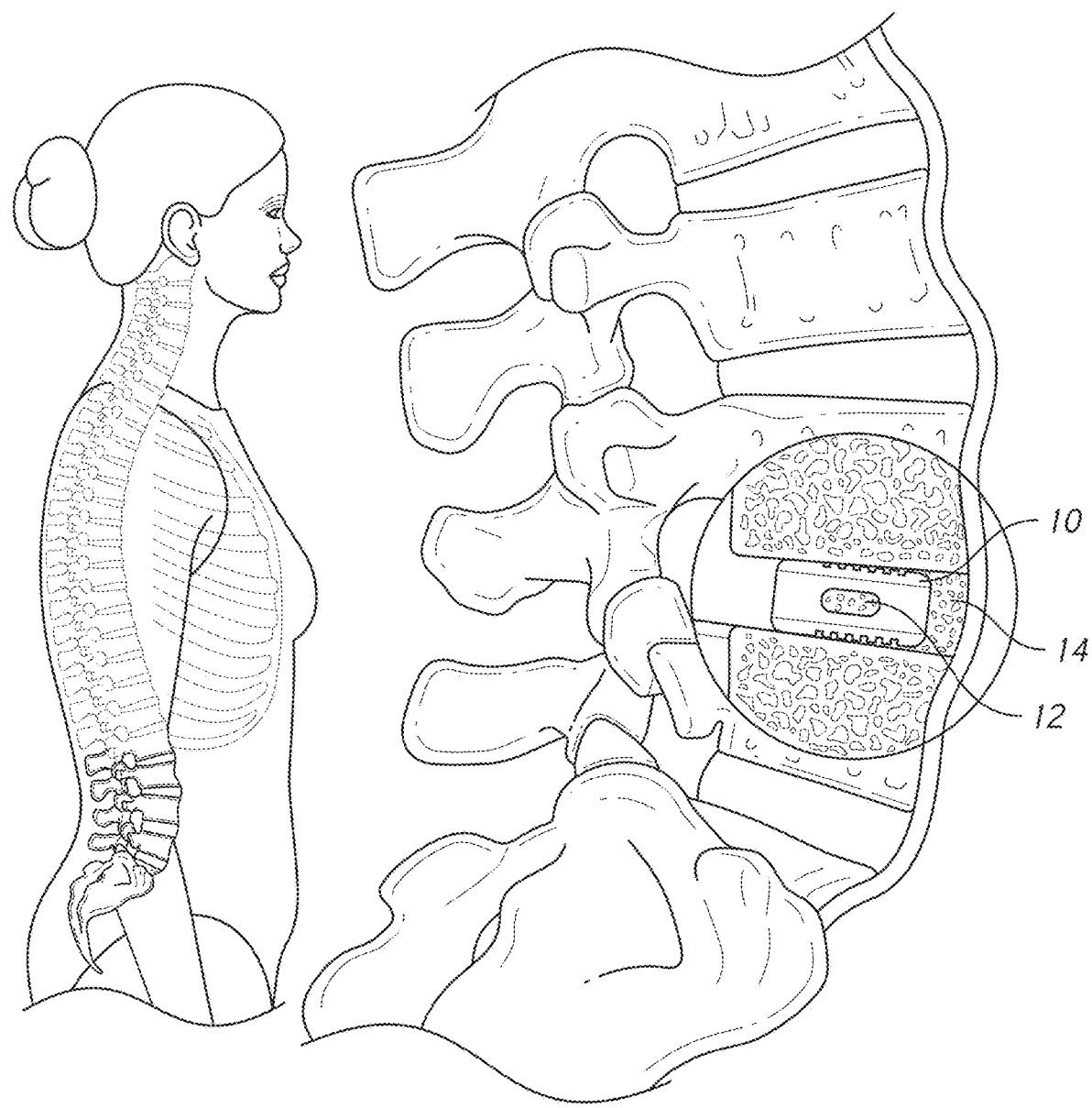
FIG. 2 is a lateral view of a vertebral column with an implant.

FIG. 2 is a lateral view of a portion of a vertebral column. During a spinal fusion procedure, the surgeon can place an implant, generally called a cage, in the disc space between two vertebrae to be fused. The cage can be inserted from a posterior, lateral, or anterior direction depending on the nature and shape of the cage selected by the surgeon. Cages can be made of plastics or metallic material, or a combination of both. In some embodiments, the cage can be generally bullet shaped in order to conform to the curvature of the endplates of the vertebrae between which the cage is inserted. As illustrated in FIG. 2, the cage can include a hole formed in a central portion of the body of the cage for receiving bone graft material to accelerate the fusion process. When deposited in the hole, the graft material comes into physical contact with the vertebral endplates above and below the cage once the cage is placed between vertebral endplates. In some methods of use, the graft material heals into a solid fused state over a period of weeks, thus bonding the endplates and their associated vertebrae permanently to one another.

A failure of the bonding of the vertebral endplates is called a non-union. Risk of non-union risk increases with increased distance between bones (gap), poor quality graft, inadequate graft quantity, motion at fusion site (inadequate fixation), and/or poor end-plate preparation (residual cartilage on end-plate and/or insufficient decortication of end-plate bone). The use of additional hardware, such as spinal screws and rods, does not necessarily lead to a successful fusion. Instead, success is often a result of exposed bone tissue in contact with good graft. Typically, bleeding bone fuses better than avascular or cortical bone.

With the cage in the disc space, there is a distraction force of the cage pushing against the vertebral endplates above and below the cage. This distractive force is countered by the fibrous tissues located at the periphery of the vertebral endplates (the annulus) which tighten and become rigid under tension. The rigidity that the cage creates in a previously mobile spinal segment is called "ligamentotaxis," and this rigidity helps fusion to develop. Bones fuse best when immobilized and stable. In some methods of use, screws, alone or in combination with spinal rods, can be inserted in the spine in addition to the cage.

Because of the distraction, the vertebral endplates exert substantial compressive force on the cage when the cage is inserted in the disc space, and vice versa such that the cage exerts a force on the vertebral endplates. If the surgeon is too aggressive when prepping the vertebral endplates, then the vertebral endplates can become weakened and the cage can subside into the endplates over time. If the surgeon is not aggressive, however, then cartilage is likely to remain on the vertebral endplates and fusion may fail, for instance, by non-union. FIG. 2 illustrates the cage 10 placed in the disc space between two lumbar vertebrae L4 and L5.

Typically, the cage 10 includes a posterior to anterior opening for the placement of bone graft 12. Another hole in the side of the cage allows the surgeon see the bone graft 12 deposited within the cage 10. In FIG. 2, the bone graft 12 deposited in the cage 10 is in contact with the L4 vertebral endplate bone above, and the L5 vertebral endplate bone below. The vertebral endplates are typically roughened by the surgeon prior to inserting the cage 10 so that raw bleeding endplate bone will come into contact with the bone graft 12 deposited in the cage 10. The roughening causes the endplates to weaken structurally, however, and consumes much surgical time to perform.

As seen in FIG. 2, besides depositing the bone graft 12 inside the cage 10, the surgeon is able to pack additional bone graft 14 into the anterior disc space before inserting the cage 10. The anterior bone graft 14 can be held in place between the body of the cage 10 and an anterior longitudinal ligament. In FIG. 2, bone graft material is not positioned posterior (to the left) of the cage 10. Surgeons typically do not place graft material in that region because there is no anatomical structure to hold the graft material in place. In addition, surgeons typically do not place graft material in that region because migration of the graft material from a position posterior to the cage can cause compression of the graft material against nerve structures that are present in the region posterior to the cage 10.

The spinal implant 10, and others described herein, can be designed to retain a substance within the opening. The substance can be bone graft material, including any osteogenic substance. The substance can be a bone graft, including autograft, dentin graft, allograft, alloplastic grafts, xenographs, or synthetic grafts. The material of artificial bone can be selected to have similar properties of the adjacent vertebrae and can comprise ceramics such as calcium phosphates, bioglass, and calcium sulfate. The material can include strontium, bone marrow, human growth factors or morphogens, bone morphogenetic proteins, or demineralized bone matrix. The bone graft can be reabsorbed or replaced with bone ingrowth as the adjacent vertebrae fuse together. The graft material can be any substance any biologic and/or chemical substance. The graft material can be any substance designed to prompt bone ingrowth or fusion. As described herein, the bone ingrowth or fusion can facilitate long-term fixation and stabilization of the adjacent vertebrae.

A study conducted by J. A. Rihn, M.D., et al. and published online in 2014, evaluates the results of disc space preparation for fusion by experienced surgeons. The study found that in most cases, the disc space preparation was inadequate. Fusion did not occur whenever cartilage remained on the endplates in the area that was prepared. The study concluded that fusion is inhibited when bone graft is confronted with cartilage that remains on the endplates. That is, unless the endplates are properly prepared by removing all of the cartilage, the middle of the disc space is not a region where fusion is predictable.

Accordingly, the risk of a non-union between adjacent vertebrae increases with (i) poor quality graft material, (ii) an inadequate quantity of graft material, (iii) motion at the fusion site due to the absence of screws or lack of ligamentotaxis, (iv) increased distance or gap between the vertebrae, and (v) poor endplate preparation, e.g., residual cartilage on the endplates and/or insufficient decortication of the endplates.

Figure 3A:
FIGS. 3A and 3B are views of the vertebral column.
Figure 3B:
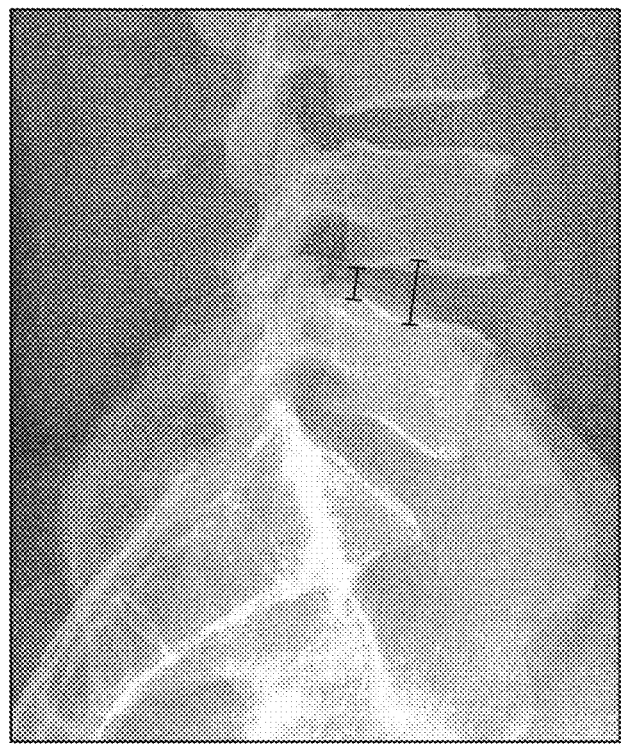

FIG. 3A is an MM lateral view of the lumbar spine, showing a sagittal cut through the center of the spine. The vertebral bones are shaped such that their endplates are concave. Because of this curvature and concavity, the endplates are closest to one another at the most posterior point, and are farthest apart at the centers of the endplates. Accordingly, the distance that a fusion must span is less if it occurs in the most posterior region of the disc, rather than in the center region where the fusion must span the greatest distance. FIG. 3B is a lateral x-ray view of the spine. The distances between the endplates of L4 and L5 at different points along the endplates are such that the greatest distance is at the midpoint of the disc, and the least distance is at the posterior aspect of the disc. FIG. 3B illustrates the different distances within the disc space. The left line illustrates the shortest distance near the edge of the vertebrae. The shortest distance may be near the cortical rim. The right line illustrates the longest distance between vertebral endplates. The longest distance may be near the center of the endplates.

The purpose of interbody fusion devices can be to restore and maintain disk space height and normal sagittal contours (lordosis), and to increase the stability of the operated segment or segments. Stability and lordosis are obtained by stretching the disc annulus and the supporting ligaments via distraction of the disk space. See, A. L. Williams, et al., "CT Evaluation of Lumbar Interbody Fusion: Current Concepts," American Journal of Neuroradiology (September 2005), vol. 26, no. 8, at pages 2057-66.

Figure 4A:
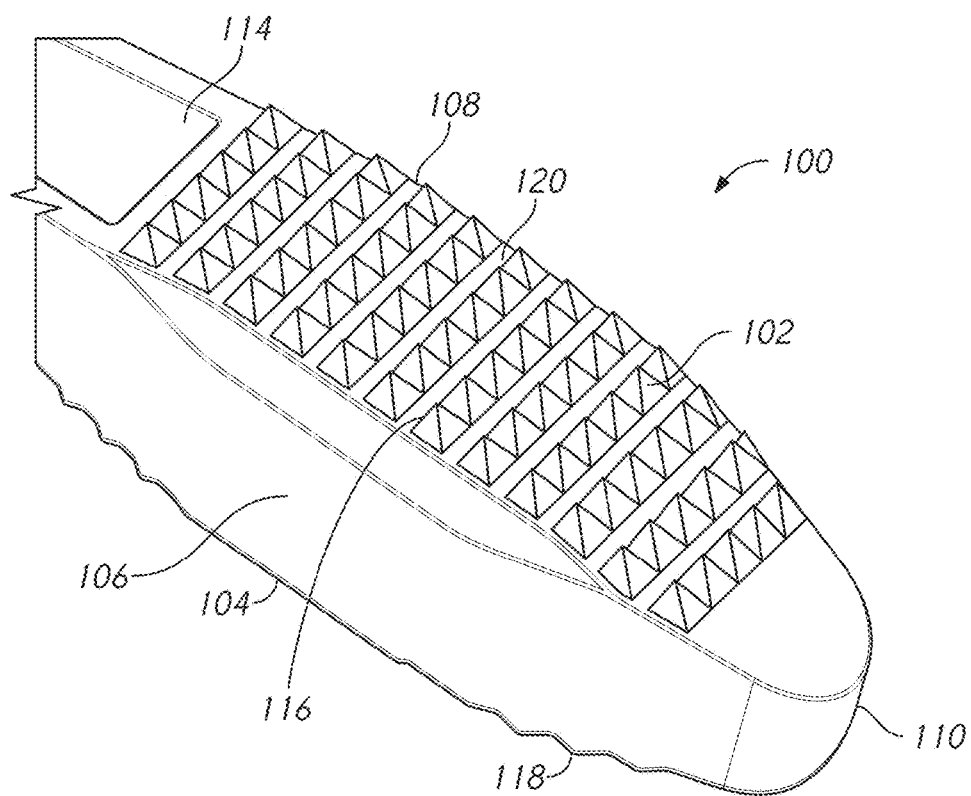
FIGS. 4A and 4B are schematic views of an embodiment of a spinal implant.
Figure 4B:
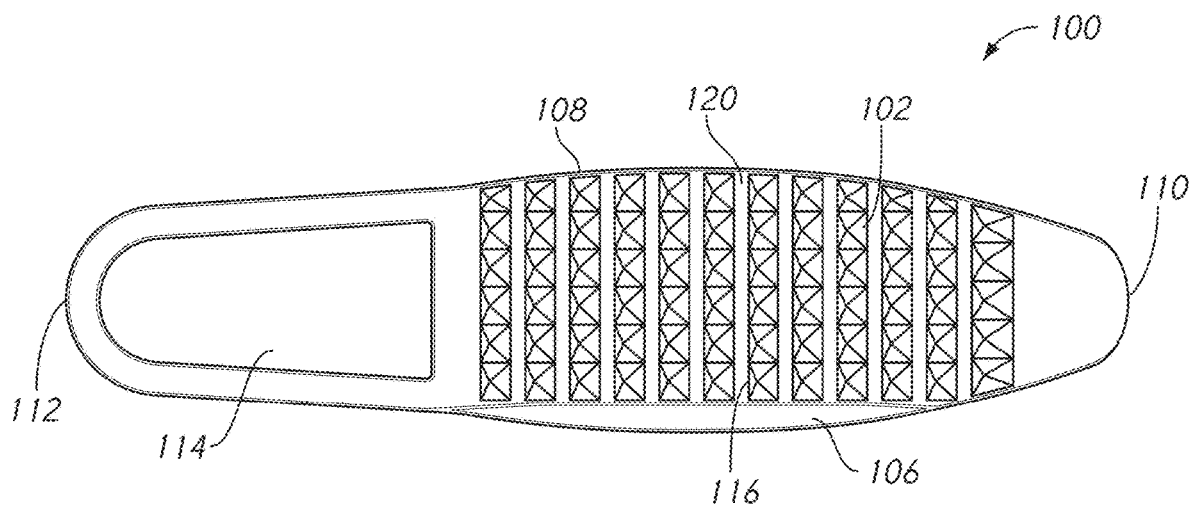

FIGS. 4A and 4B are schematic views of an embodiment of a spinal implant 100. The spinal implant 100 can include an upper surface 102. The upper surface 102 can be designed to contact an upper vertebral endplate when the spinal implant 100 is disposed within the intervertebral disc space. The spinal implant 100 can include a lower surface 104. The lower surface 104 can be designed to contact a lower vertebral endplate when the spinal implant 100 is disposed within the intervertebral disc space. The spinal implant 100 can include two side surfaces 106, 108. The two side surfaces 106, 108 can extend between the upper surfaces 102 and lower surface 104. The two side surfaces 106, 108 can extend along the length of the spinal implant 100. The two side surfaces 106, 108 can define the height of the spinal implant. The two side surfaces 106, 108 can be designed to generally match the height of the intervertebral disc space between the adjacent vertebrae. As described herein, the spinal implant can be expandable in height. As described herein, the spinal implant can be expandable in width. The spinal implant can be static in dimension or expandable in at least one dimension.

The spinal implant 100 can include a front surface 110. The front surface 110 can extend between the upper surfaces 102 and lower surface 104, or a portion thereof. In some embodiments, the front surface 100 can be inserted first into the intervertebral disc space between the adjacent vertebrae. The front surface 110 can include features to facilitate insertion such as a rounded surface. In some embodiments, the front surface 110 can be tapered inward from the two side surfaces 106, 108. In some embodiments, the front surface 110 can have a reduced height from the two side surfaces 106, 108.

The spinal implant 100 can include a back surface 112. The back surface 112 can extend between the upper surfaces 102 and lower surface 104, or a portion thereof. In some embodiments, the back surface 112 can be inserted last into the intervertebral disc space between the adjacent vertebrae. The back surface 112 can include features to retain a graft material as described herein. In some embodiments, the back surface 112 can be tapered inward from the two side surfaces 106, 108. In some embodiments, the back surface 112 can have a reduced height from the two side surfaces 106, 108.

The spinal implant 100 can include an opening 114. The opening 114 can extend between the upper surfaces 102 and lower surface 104, or a portion thereof. The opening 114 can extend between the vertebrae when the spinal implant 100 is inserted between adjacent vertebrae. The opening 114 can extend generally vertically within the patient when the spinal implant 100 is inserted between adjacent vertebrae. In some embodiments, the opening 114 is adjacent to the back surface 112. In some embodiments, the opening 114 is adjacent to a portion of the two side surfaces 106, 108. In some embodiments, the opening 114 is enclosed. The opening 114 can be enclosed by the back surface 112 and at least a portion of the two side surfaces 106, 108. The opening 114 is positioned such that it is located away from the center of the spinal implant 100. In some embodiments, the opening 114 is located near the very end of the spinal implant 100. In some embodiments, the opening 114 is located posteriorly when the implant is inserted in an anterior/posterior direction. In some embodiments, the opening 114 is located laterally when the implant is inserted in a lateral direction. In some embodiments, the opening 114 is located opposite the insertion end of the spinal implant 100.

The opening 114 can form a void in the top surface 102 and the bottom surface 104. The opening 114 can be described in terms of the surface area. In some embodiments, the opening 114 can be at least 5% of the surface area of the top surface 102 or the bottom surface 104. In some embodiments, the opening 114 can be at least 10% of the surface area of the top surface 102 or the bottom surface 104. In some embodiments, the opening 114 can be at least 15% of the surface area of the top surface 102 or the bottom surface 104. In some embodiments, the opening 114 can be at least 20% of the surface area of the top surface 102 or the bottom surface 104. In some embodiments, the opening 114 can be at least 25% of the surface area of the top surface 102 or the bottom surface 104. In some embodiments, the opening 114 can be at least 30% of the surface area of the top surface 102 or the bottom surface 104. In some embodiments, the opening 114 can be at least 35% of the surface area of the top surface 102 or the bottom surface 104. In some embodiments, the opening 114 can be at least 40% of the surface area of the top surface 102 or the bottom surface 104. In some embodiments, the opening 114 can be at least 45% of the surface area of the top surface 102 or the bottom surface 104. In some embodiments, the opening 114 can be at least 50% of the surface area of the top surface 102 or the bottom surface 104.

In some embodiments, the opening 114 can be between 0% and 20% of the surface area of the top surface 102 or the bottom surface 104. In some embodiments, the opening 114 can be between 10% and 30% of the surface area of the top surface 102 or the bottom surface 104. In some embodiments, the opening 114 can be between 20% and 40% of the surface area of the top surface 102 or the bottom surface 104. In some embodiments, the opening 114 can be between 30% and 50% of the surface area of the top surface 102 or the bottom surface 104. In some embodiments, the opening 114 can be a range between any two of the foregoing percentages of the surface area of the top surface 102. In some embodiments, the opening 114 can be a range between any two of the foregoing percentages of the surface area of the bottom surface 104.

The opening 114 can form a void along the length of the spinal implant 100. The opening 114 can be described in terms of the length. In some embodiments, the opening 114 can be at least 5% of the length of the spinal implant 100. In some embodiments, the opening 114 can be at least 10% of the length of the spinal implant 100. In some embodiments, the opening 114 can be at least 15% of the length of the spinal implant 100. In some embodiments, the opening 114 can be at least 20% of the length of the spinal implant 100. In some embodiments, the opening 114 can be at least 25% of the length of the spinal implant 100. In some embodiments, the opening 114 can be at least 30% of the length of the spinal implant 100. In some embodiments, the opening 114 can be at least 35% of the length of the spinal implant 100. In some embodiments, the opening 114 can be at least 40% of the length of the spinal implant 100. In some embodiments, the opening 114 can be at least 45% of the length of the spinal implant 100. In some embodiments, the opening 114 can be at least 50% of the length of the spinal implant 100.

In some embodiments, the opening 114 can be between 0% and 20% of the length of the spinal implant 100. In some embodiments, the opening 114 can be between 10% and 30% of the length of the spinal implant 100. In some embodiments, the opening 114 can be between 20% and 40% of the length of the spinal implant 100. In some embodiments, the opening 114 can be between 30% and 50% of the length of the spinal implant 100. In some embodiments, the opening 114 can be a range between any two of the foregoing of the lengths of the spinal implant 100.

The opening 114 can have a diameter or cross-sectional dimension. The diameter or cross-sectional dimension can be taken along the width between the side surfaces 106, 108. In some embodiments, the opening 114 can be at least 50% of the width of the spinal implant 100. In some embodiments, the opening 114 can be at least 60% of the width of the spinal implant 100. In some embodiments, the opening 114 can be at least 70% of the width of the spinal implant 100. In some embodiments, the opening 114 can be at least 80% of the width of the spinal implant 100. In some embodiments, the opening 114 can be at least 90% of the width of the spinal implant 100. In some embodiments, the opening 114 can be at least 100% of the width of the spinal implant 100. In some embodiments, the opening 114 can have a diameter or cross-sectional dimension of 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, at least 5 mm, at least 8 mm, at least 10 mm, at least 12 mm, between 8 and 12 mm, between 5 and 20 mm, or any range of the foregoing values. The opening 114 can be free or substantially free from any intervening structures. The opening 114 can be free or substantially free from any structures across the width of the opening 114. The opening 114 can be free or substantially free from any structures along the height of the opening 114. The opening 114 can be free or substantially free from any structures along the length of the opening 114. The opening 114 can be free or substantially free from any structures along the top surface or bottom surface of the opening 114.

In some embodiments, the spinal implant 100 can provide access, endplate to endplate, of graft material having a diameter or cross-sectional dimension of 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, at least 5 mm, at least 8 mm, at least 10 mm, at least 12 mm, between 8 and 12 mm, between 5 and 20 mm, or any range of the foregoing values. In some embodiments, the opening 114 surrounds the graft material on four sides. In some embodiments, the opening 114 surrounds the graft material on three sides.

Figure 6A:
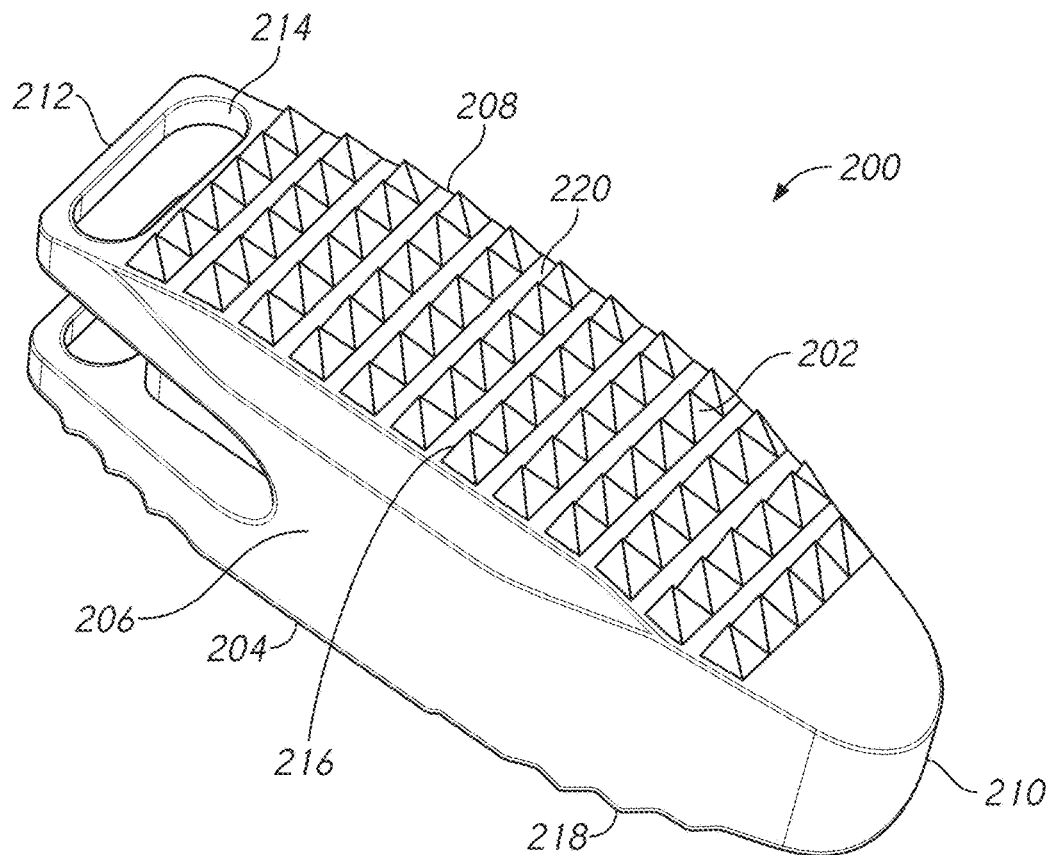
FIGS. 6A and 6B are schematic views of an embodiment of a spinal implant.

In some embodiments, the opening 114 is oblong or elongate. In some embodiments, the opening 114 is round. In some embodiments, the opening 114 is rectangular, square, or polygonal. In some embodiments, the opening 114 can include a longitudinal axis. In some embodiments, the longitudinal axis is the longest axis of the opening 114. The longitudinal axis can be along the length of the opening 114, as shown in FIG. 4A. In some embodiments, the longitudinal axis can be along the width of the opening 114, as shown in FIG. 6A. In some embodiments, the longitudinal axis can be along the height of the opening 114.

In some embodiments, the upper surface 102 can include one or more features to promote engagement between the spinal implant 100 and the upper vertebral endplate. The upper surface 102 can include projections 116 which extend from the upper surface 102. The projections 116 can be arranged in any pattern such as the grid as shown in FIGS. 4A and 4B. In some embodiments, the lower surface 104 can include one or more features to promote engagement between the spinal implant 100 and the lower vertebral endplate. The lower surface 102 can include projections 118 which extend from the lower surface 104. The projections 118 can be arranged in any pattern such as the grid. In some embodiments, the projections 116, 118 are the same in shape, arrangement, and/or configuration. In some embodiments, the projections 116, 118 are different in shape, arrangement, and/or configuration. In some embodiments, the spinal implant 100 has an axis of symmetry such that the spinal implant 100 can be inserted with the upper surface 102 facing either the upper endplate or the lower endplate. In some embodiments, the spinal implant 100 is designed to be inserted in a single orientation such that the upper surface 102 facing only the upper endplate.

In some embodiments, the spinal implant 100 includes only one opening 114. In some embodiments, the spinal implant 100 consists of one opening 114. In some embodiments, the spinal implant 100 includes only one opening 114 designed to accept bone graft. In some embodiments, the spinal implant 100 consists of one bone graft opening 114.

In some embodiments, the opening 114 is adjacent to the back surface 112 of the spinal implant 100. In some embodiments, the opening 114 is contiguous with the back surface 112. In some embodiments, the opening 114 is placed relative to an edge of the spinal implant 100. In some embodiments, the opening 114 is placed relative to a posterior edge of the spinal implant 100, as described herein.

In some embodiments, the opening 114 is offset from the center of the length of the spinal implant 100. The center of the spinal implant 100 can be located halfway between the front surface 110 and the back surface 112. The center of the spinal implant 100 can be located halfway along the length of the spinal implant 100. In some embodiments, the opening 114 is located closer to the back surface 112 than the front surface 110. In some embodiments, the opening 114 is located adjacent to the back surface 112.

In some embodiments, the opening 114 is centered along the width of the spinal implant 100. The center of the width of the spinal implant 100 can be located halfway between the side surfaces 106, 108. The opening 114 can be located between the side surfaces 106, 108. In some embodiments, the opening 114 is centered along the height of the spinal implant 100. The center of the height of the spinal implant 100 can be located halfway between the top surface 102 and the bottom surface 104. The opening 114 can be located between the top surface 102 and the bottom surface 104.

In some embodiments, the spinal implant 100 can form a solid body 120. The solid body 120 can extend from the front surface 110 to the opening 114. The solid body 120 can extend from the top surface 102 to the bottom surface 104. The solid body 120 can extend between the side surfaces 106, 108. In some embodiments, the solid body 120 can be without an opening. In some embodiments, the solid body 120 can be continuous. In some embodiments, the solid body 120 can be substantially solid or substantially rigid. In some embodiments, the solid body 120 can be any form to withstand the compressive forces of the vertebrae.

The solid body 120 can be described in terms of the surface area. In some embodiments, the solid body 120 can be at least 50% of the surface area of the top surface 102 or the bottom surface 104. In some embodiments, the solid body 120 can be at least 55% of the surface area of the top surface 102 or the bottom surface 104. In some embodiments, the solid body 120 can be at least 60% of the surface area of the top surface 102 or the bottom surface 104. In some embodiments, the solid body 120 can be at least 65% of the surface area of the top surface 102 or the bottom surface 104. In some embodiments, the solid body 120 can be at least 70% of the surface area of the top surface 102 or the bottom surface 104. In some embodiments, the solid body 120 can be at least 75% of the surface area of the top surface 102 or the bottom surface 104. In some embodiments, the solid body 120 can be at least 80% of the surface area of the top surface 102 or the bottom surface 104. In some embodiments, the solid body 120 can be at least 85% of the surface area of the top surface 102 or the bottom surface 104. In some embodiments, the solid body 120 can be at least 90% of the surface area of the top surface 102 or the bottom surface 104. In some embodiments, the solid body 120 can be at least 95% of the surface area of the top surface 102 or the bottom surface 104.

In some embodiments, the solid body 120 can be between 50% and 70% of the surface area of the top surface 102 or the bottom surface 104. In some embodiments the solid body 120 can be between 60% and 80% of the surface area of the top surface 102 or the bottom surface 104. In some embodiments, the solid body 120 can be between 70% and 90% of the surface area of the top surface 102 or the bottom surface 104. In some embodiments, the solid body 120 can be a range between any two of the foregoing percentages of the surface area of the top surface 102. In some embodiments, the solid body 120 can be a range between any two of the foregoing percentages of the surface area of the bottom surface 104.

The solid body 120 can be described in terms of the surface length. In some embodiments, the solid body 120 can be at least 50% of the length of the spinal implant 100. In some embodiments, solid body 120 can be at least 55% of the length of the spinal implant 100. In some embodiments, solid body 120 can be at least 60% of the length of the spinal implant 100. In some embodiments, solid body 120 can be at least 65% of the length of the spinal implant 100. In some embodiments, solid body 120 can be at least 70% of the length of the spinal implant 100. In some embodiments, solid body 120 can be at least 75% of the length of the spinal implant 100. In some embodiments, solid body 120 can be at least 80% of the length of the spinal implant 100. In some embodiments, solid body 120 can be at least 85% of the length of the spinal implant 100. In some embodiments, solid body 120 can be at least 90% of the length of the spinal implant 100. In some embodiments, the solid body 120 can be at least 95% of the length of the spinal implant 100.

In some embodiments, the solid body 120 can be between 50% and 70% of the length of the spinal implant 100. In some embodiments, the solid body 120 can be between 60% and 90% of the length of the spinal implant 100. In some embodiments, the solid body 120 can be between 70% and 100% of the length of the spinal implant 100. In some embodiments, the solid body 120 can be a range between any two of the foregoing of the lengths of the spinal implant 100.

In some embodiments, a hole or opening (not shown) can be formed in a central region of the cage body for reasons other than depositing bone graft material. In some embodiments, a central opening can be provided for certain mechanical or structural considerations, or to facilitate the manufacture of the cage. In some embodiments, the spinal implant 100 can be formed from 3D printing. In some embodiments, the spinal implant 100 can include a porous construct with micro holes throughout the spinal implant 100. In some methods of use, a solid spinal implant (without a central hole) can exert too much pressure on the endplates. In some methods of use, a solid spinal implant can cause increased pressure in the vertebral bones, leading to back pain. In some methods of use, a solid spinal implant may have to be removed because of back pain. In some methods of use, after removal of the spinal implant, the pain was reduced. In some embodiments, the spinal implant described herein can include a central hole or opening to reduce pressure on the vertebral endplates. In some methods of use, this central hole is not utilized for graft material. Rather, the central hole can be designed to reduce the pressure exerted on the vertebral endplates. In some embodiments, the spinal implant is not limited to designs with one or more openings at the far periphery of the spinal implant. In some embodiments and methods of use, there may be a need to keep a central opening, for instance to reduce pressure forces. In some embodiments, pressure is reduced by one opening, such as a centrally located opening. In some embodiments, the spinal implant includes one or more opening, such as multiple small central holes to reduce pressure. In some embodiments, the spinal implant includes only one opening for graft material located near the end of the spinal implant. In some embodiments, the spinal implant includes only two openings for graft material, each located an end of the spinal implant. In some embodiments, each end of the spinal implant includes an opening for graft material. In some embodiments, the spinal implant can include one or more additional openings to reduce pressure on the vertebral endplates. In some embodiments, the spinal implant can include one or more additional openings which are not designed to accommodate graft material.

In some methods of use, the opening 114 can be designed to contact the cortical rim when the spinal implant 100 is disposed between the vertebrae. A cortical rim is found on both the upper and lower vertebral bodies. Both the upper endplate and the lower endplate of the vertebra are concave. In some methods of use, a tool is used to decorticate the elevated rim from both endplates, see FIG. 20A. For example, when doing a L4-L5 fusion, the tool would scrape the cortical rim from the lower endplate of the upper vertebra (L4) and the upper endplate of the lower vertebra (L5). When the implant is positioned, the opening 114 can contain graft material that spans between a cortical rim of the upper vertebral body and a cortical rim of the lower vertebral body. In methods of use where the cortical rim is decorticated, the opening 114 is placed adjacent to a decorticated cortical rim of the upper vertebral body and a decorticated cortical rim of the lower vertebral body. The opening 114 can be packed with bone graft designed to promote fusion between adjacent vertebrae. As described herein, the height between adjacent vertebral endplates can be smallest adjacent to the cortical rim. As described herein, the height between adjacent vertebral endplates can be largest near the concave center of the vertebral endplates. The vertebral endplates can include a curvature such that the height increases near the center of the intervertebral disc space.

The spinal implant 100 can be generally shaped to match the natural anatomy of the vertebral endplates. In some embodiments, the height of the spinal implant 100 can vary from a larger dimension for the solid body 120 and a smaller dimension for the opening 114. In some embodiments, the two side surfaces 106, 108 can taper from a center of the spinal implant 100 to the front surface 110. In some embodiments, the two side surfaces 106, 108 can taper from a center of the spinal implant 100 to the back surface 112.

The spinal implant 100 can increase in height along the length of the spinal implant. In particular, the distance between the upper surface 102 and the lower surface 104 can increase near the center of the length of the spinal implant 100. This increase in height can facilitate spinal fusion by filling the space between the adjacent vertebrae. The height of the spinal implant 100 can be designed to restore the natural height between adjacent vertebrae. In this embodiment, the spinal implant 100 can exert a compressive force on adjacent vertebra. In some embodiments, the solid body 102 contacts adjacent vertebral bodies. The solid body 120 can be designed to exert a compressive force on the vertebral endplates. In some embodiments, the solid body 102 can be designed to match the curvature of the vertebral endplates.

In some embodiments, the solid body 120 can comprise a strong material capable of withstanding the compressive force of the vertebrae. The solid body 120 can comprise any biomaterial. The solid body 120 can be manufactured from, including but not limited to, a metal, a ceramic, a polymer, or a combination of two or more of these materials. Examples of plastics include polyetheretherketone (PEEK), polyetherketoneketone (PEKK), polyethylene, or fluoropolymer; examples of ceramics include zirconia or silicon nitride; and examples of metals include titanium, titanium-aluminium-vanadium, nitinol, or stainless steel.

In some embodiments, the back surface 112 and/or a portion of the side surfaces 106, 108 can be formed of the same material as the solid body 120. In some embodiments, the entire spinal implant 100 is formed of the same material. In some embodiments, the spinal implant 100 is monolithically formed. In some embodiments, the spinal implant 100 is unitary. In some embodiments, the spinal implant 100 is integrally formed. In some embodiments, the spinal implant 100 includes at least a portion that is over molded.

In some embodiments, the back surface 112 and/or a portion of the side surfaces 106, 108 can be formed of a different material that the solid body 120. In some embodiments, the portion of the spinal implant 100 which forms the opening 114 is formed of a different material than the solid body 120. In some embodiments, the portion of the spinal implant 100 which forms the opening 114 is formed of a softer, more malleable material. The material can be more elastic. The material can be compressible by the cortical rim. In some embodiments, the portion of the spinal implant 100 which forms the opening 114 is collapsible. In some embodiments, at least a portion of the edge of opening 114 is configured to collapse after implantation. In some embodiments, at least a portion of the edge of the opening 114 is more flexible. The portion of the spinal implant 100 which forms the opening 114 can comprise any biomaterial. The portion of the spinal implant 100 which forms the opening 114 can be manufactured from, including but not limited to, a metal, a ceramic, a polymer, or a combination of two or more of these materials.

As described herein, the opening 114 for depositing bone graft material is formed in the spinal implant 100. The position of the opening 114 can be located at a far end portion of the spinal implant 100 rather than at the center of the spinal implant 100. By placing the opening 114 away from the central region of the spinal implant 100, the solid body 120 of the spinal implant 100 can provide a maximal surface area against the vertebral endplates. In some embodiments, the solid body 120 does not comprise any through holes formed in the solid body 120. The middle of the spinal implant 100 is rigid or substantially rigid. The solid body 120 can provide maximal distraction of the disc space with little if any stress points. With a larger effective surface area, the solid body 120 of the spinal implant 100 diffuses the distractive force across the entire area of contact between the spinal implant 100 and the vertebral endplates so that there is less chance of subsidence. In some embodiments, the spinal implant 100 can allow all the area of the spinal implant 100 located within the center region of the disc space to provide ligamentotaxis while reducing the risk of subsidence.

As described herein, the opening 114 can be configured to retain bone graft or other fusion promoting materials. The opening 114 can be offset from the solid body 120. During positioning, the opening 114 can be located along the cortical rim. In some methods, the portion of the spinal implant 100 which forms the opening 114 can be the last portion of the spinal implant 100 to be inserted within the disc space. The cortical rim is located near the edge of the vertebral body, and is therefore easily prepared for fusion. The cortical rim can be easily inspected by the surgeon prior to placement of the spinal implant 100. As described herein, the spinal implant 100 can be designed for fusion to occur in an area of the disc space that is easy for the surgeon to prepare effectively.

There are many advantages associated with the spinal implant 100. In some methods of use, there is a shorter distance for a fusion to span. That is, it can be better to fuse the vertebral bones at a position where the bones are closest to one another, i.e., at the periphery of the associated disc. The spinal implant 100 can include the opening 114 positioned at the periphery of the spinal implant 100. When inserted into the disc space, the spinal implant 100 can be positioned such that the opening 114 is near the cortical rim. The cortical rim is typically the location at which the vertebral endplates are closest. The cortical rim is also where the disc space is narrowest. In some embodiments, the fusion requires less bone graft material. In some embodiments, the fusion requires occurs over a shorter distance at the cortical rim than the center of the vertebral endplates. In some embodiments, the fusion is faster. In some embodiments, the fusion is stronger. In some embodiments, the fusion is more predictable by leading to more favorable outcomes, more often.

In some methods of use, the spinal implant 100 is placed without weakening of the central regions of the endplates. In some methods of use, there is no need to decorticate the vertebral endplates other than at the entrance to the disc space for insertion of the spinal implant 100. The vertebral endplates can remain intact. The solid body 120 can support the vertebral endplates to restore the height of the disc space. In some methods of use, fusion does not occur in the central regions of the endplates. Rather, fusion can occur at the cortical rim. In some methods of use, the cortical rim is decorticated. This can facilitate insertion of the spinal implant 100 and/or facilitate fusion of the bone graft. The cortical rim is easier to decorticate because this bone is located at the periphery of the disc space which is within easy reach.

In some methods of use, the spinal implant 100 can facilitate quicker surgery time, including the time the patient is in the operating room. In some methods of use, there is no need for extensive disc space cleaning. In some methods of use, the surgeon need only remove enough disc material to make room for the spinal implant to be inserted. The preparation of the vertebral endplate may not be necessary.

As described herein, the spinal implant 100 can include an elongated body in which the opening 114 for depositing graft material is formed at an end portion of the spinal implant 100. This opening 114 can allow the deposited graft to be situated at the most narrow region of the disc space, and where the vertebral endplates are most easily and best decorticated.

The spinal implant 100 can be sized according to the corresponding adjacent vertebrae. The spinal implant 100 can be sized according to the patient. The length of the spinal implant 100 extends from the front surface 110 to the back surface 112. The width of the spinal implant 100 extends between the two side surfaces 106, 108. The height of the spinal implant 100 extends between the upper surface 102 and the lower surface 104. In some embodiments, the length of the spinal implant 100 is typically at least two times the width of the spinal implant 100 (e.g., three times, four times, five times, six times, seven times, eight times, nine times, ten times, etc.). In some embodiments, the length of the spinal implant 100 is typically at least two times the height of the spinal implant 100 (e.g., three times, four times, five times, six times, seven times, eight times, nine times, ten times, etc.). In some embodiments, the width of the spinal implant 100 is greater than the height of the spinal implant 100, but other configurations are contemplated. The spinal implant 100 can be sized 1 to 2 cm longer than a typical cage so that the opening 114 can be situated at the periphery of the disc space. The dimensions of the spinal implant 100 can vary based on the insertion direction of the spinal implant 100. For instance, the spinal implant 100 that is configured to be inserted from a lateral direction can be longer than the spinal implant 100 that is configured to be inserted from a posterior direction. This change in length can be due to the natural geometry of the vertebrae, wherein the lateral dimension of the vertebrae is greater than the anterior/posterior dimension.

Figure 5:
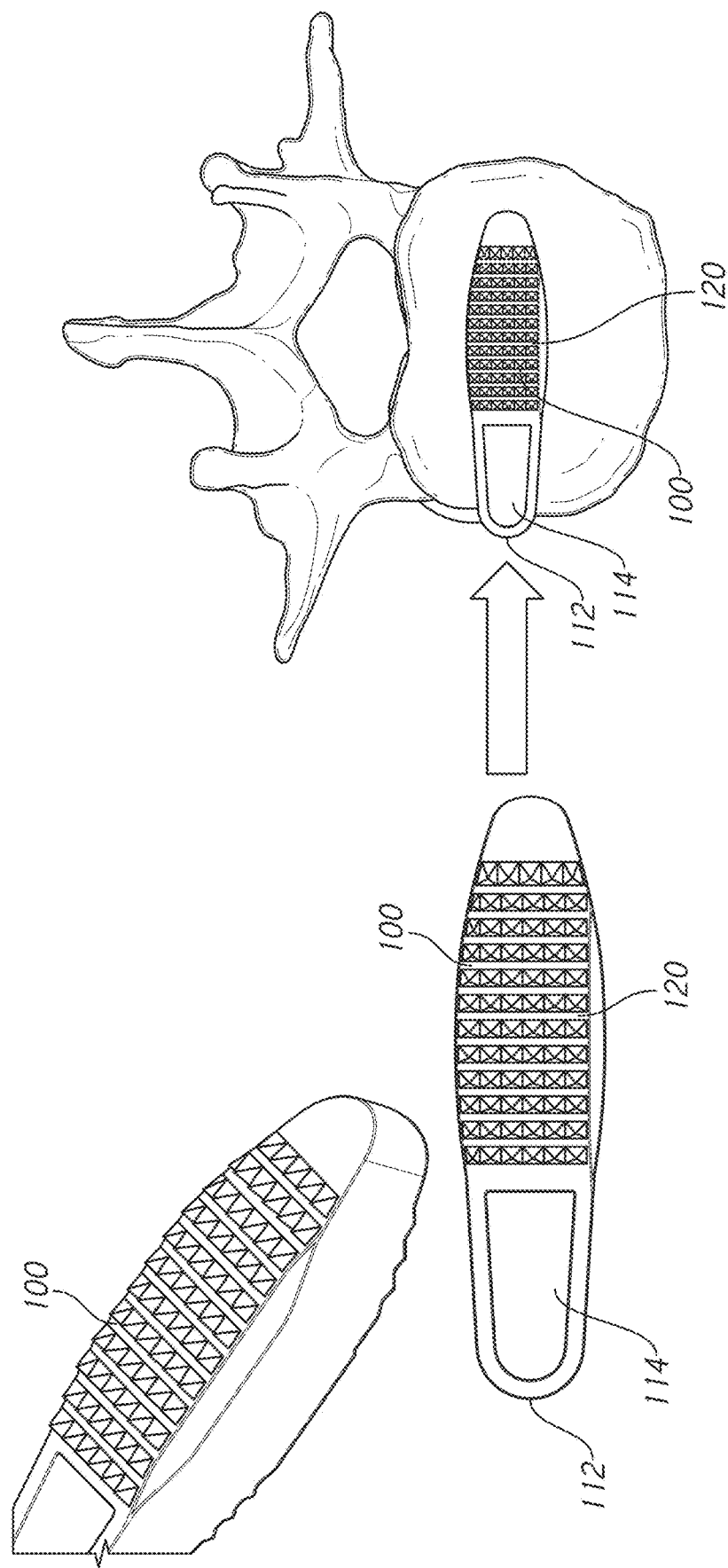
FIG. 5 is a schematic view of a placement of the spinal implant of FIG. 4A.

FIG. 5 is a schematic view of a placement of the spinal implant of FIG. 4A. In some methods of use, the spinal implant 100 is inserted from a lateral direction. The opening 114 can be positioned adjacent to the cortical rim such that the opening 114 spans the shortest distances between vertebral endplates. As described herein, the spinal implant 100 can be inserted from a posterior, lateral, oblique, or anterior direction. FIG. 5 illustrates various features of the vertebra for reference including the spinous process, the superior articular facet, the superior articular process, the lamina, the transverse process, the pedicle, and the vertebral foramen. The opening 114 for graft is in contact with the cortical rim area of the vertebral bone. The center of the spinal implant 100 is solid so there is more surface area of the solid body 120 in contact with the weaker cancellous bone. There is a cortical rim on the outside edge of the bone. The cortical rim is elevated whereas the endplate formed form cancellous bone is concave. The spinal implant 100 can generally match the natural curvature of the anatomy by varying the height of the spinal implant. The cortical rim or epiphyseal rim is a thin ring of smooth, cortical bone surrounding the vertebral body. The cortical rim can be a narrow bony ring which provides a location for anchoring of the intervertebral disc.

In some methods, the spinal implant 100 is inserted through a transforaminal lumbar interbody fusion (TLIF) procedure. In some methods, the spinal implant 100 is inserted through a posterior lumbar interbody fusion (PLIF) procedure. In some methods, the spinal implant 100 is inserted through a lateral or oblique interbody fusion (XLIF or OLIF) procedure. In some methods, the spinal implant 100 is inserted through an anterior lumbar interbody fusion (ALIF) procedure. In some methods, the spinal implant 100 allows for anterior, lateral, or oblique placement between the vertebrae. In some methods, only one spinal implant 100 is placed between adjacent vertebrae. In some methods, one or more spinal implants 100 are placed between adjacent vertebrae (e.g., one, two, three, or four). The spinal implant 100 can be dimensioned such that the opening 114 can be situated at the periphery of the disc space. The spinal implant 100 near the opening 114 can define a height corresponding to the distance between adjacent vertebrae near the cortical rim. The spinal implant 100 near the opening 114 can define a height corresponding to the minimum distance between adjacent vertebrae near the cortical rim. The spinal implant 100 near the opening 114 can be tapered from the maximum height of the spinal implant 100. The spinal implant 100 near the opening 114 can have a maximum height between 0 mm and 10 mm, for example 0 mm, 1 mm, 2 mm, 3 mm, 4 mm, 5 mm, 6 mm, 7 mm, 8 mm, 9 mm, 10 mm, between 5 mm and 10 mm, between 7 mm and 10 mm, between 2 mm and 7 mm, between 0 mm and 5 mm, or any range of two of the foregoing values.

The solid body 120 can define a height corresponding to the distance between adjacent vertebrae near the center of the endplates. The solid body 120 can define a height corresponding to the maximum distance between adjacent vertebrae near the center of the endplates. The solid body 120 can have a maximum height between 5 mm and 20 mm, for example 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, between 5 mm and 10 mm, between 10 mm and 15 mm, between 5 mm and 15 mm, or between 7 mm and 14 mm, or any range of two of the foregoing values.

The spinal implant 100 can include a length to span the vertebral body between opposing edges of the cortical rim, for instance, in embodiments with more than one opening for graft material. The spinal implant 100 can include a length to span a portion of the vertebral body from the cortical rim, inward, for instance in embodiments with only one opening for graft material. The spinal implant 100 can include a length to span from the cortical rim to a point beyond the midpoint of the vertebral body. The spinal implant 100 can include a length between 20 mm and 40 mm, for example 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, between 20 mm and 30 mm, between 30 mm and 40 mm, between 25 mm and 30 mm, or between 35 mm and 40 mm, or any range of two of the foregoing values.

In some embodiments, the length spinal implant 100 can be at least 50% of the distance between the opposing edges of the cortical rim. In some embodiments, the length spinal implant 100 can be at least 60% of the distance between the opposing edges of the cortical rim. In some embodiments, the length spinal implant 100 can be at least 70% of the distance between the opposing edges of the cortical rim. In some embodiments, the length spinal implant 100 can be at least 80% of the distance between the opposing edges of the cortical rim. In some embodiments, the length spinal implant 100 can be at least 90% of the distance between the opposing edges of the cortical rim. In some embodiments, the length spinal implant 100 can be at least 100% of the distance between the opposing edges of the cortical rim. In some embodiments, the length spinal implant 100 can be at least 110% of the distance between the opposing edges of the cortical rim.

In other cage designs, the spinal implant is positioned in the concave area with the hole for graft in the center of the spinal implant so that the graft comes into contact only with the concave vertebral endplates. In other cage designs, there is no bone graft in contact with the cortical rim. Unlike other cage designs, the spinal implant 100 positions the bone graft adjacent to the cortical rim. The spinal implant 100 can allow for part of the spinal implant 100, e.g., the solid body 120, to be positioned in the concave portion. However, the opening 114 for bone graft is on the far end of the spinal implant 100. The positioning of the opening 114 relative to the solid body 120 allows the graft material to come into contact with the cortical rim. As described herein, the cortical rim is an area easy to decorticate, wherein complete decortication leads to better fusion. In some embodiments, the spinal implant 100 does not have a hole in the center. The solid body 120 can be continuous. The solid body 120 is an additional advantage because there is more surface area of the spinal implant 100 in contact with the relatively weak concave endplate bone. This can help to prevent the spinal implant 100 from subsiding and can allow for more stability. In some methods, these advantages can lead to a higher chance of successful fusion.

In some embodiments, the material of the opening 114 does not have to be the same material as the rest of the spinal implant 100. In some embodiments, the sides of the opening 114 can be a softer and more malleable material (such as silastic or thin metal) so that the sides can collapse a few millimeters as the spinal implant 100 settles in place after surgery during the month's long healing phase. Such collapse would allow there to be a compressive force on the bone graft within the opening 114. This slight collapse is desirable because bone tends to heal better under compression. Wolff's Law dictates that bone does not heal well when shielded from stress.

In some methods of use, the vertebral endplates apply compressive forces against the center portion of the spinal implant 100 (ligamentotaxis). In some methods of use, the portion which extends to the periphery of the disc (the area near the opening 114) may not necessarily have a structurally supportive function. In some methods of use, the spinal implant 100 is made to mimic the modulus of elasticity of normal bone. In some embodiments, the solid body 120 or the center portion of the spinal implant 100 can have the quality of mimicking bone. In some embodiments, the area at the ends of the spinal implant 100, near the opening 114, can be more elastic than normal bone.

Figure 6B:
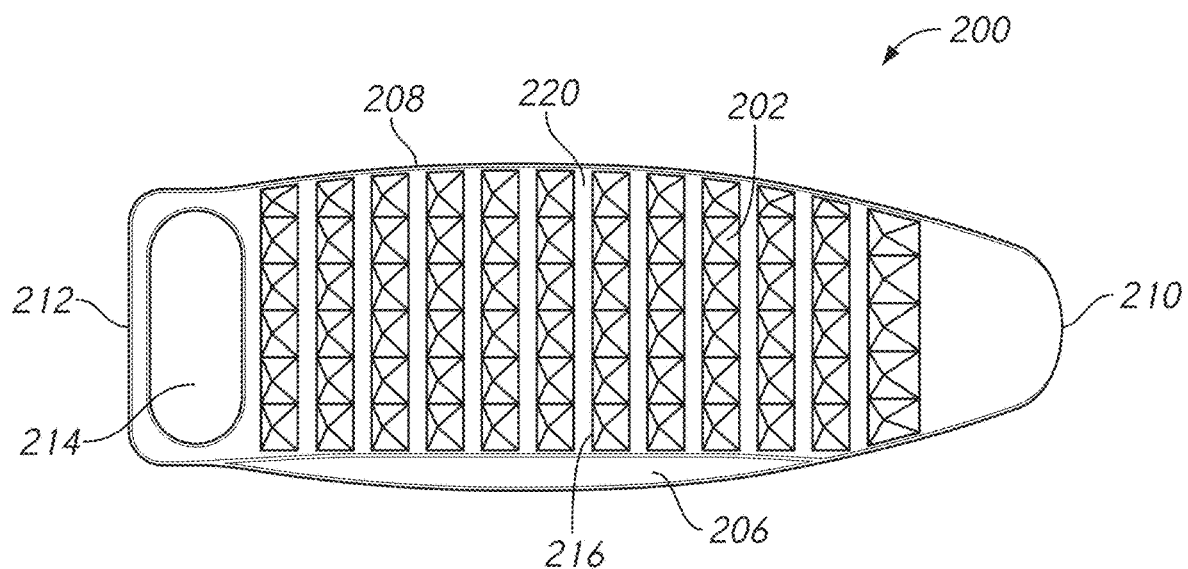

FIGS. 6A and 6B are schematic views of an embodiment of a spinal implant 200. The spinal implant 200 can include any of the features of the spinal implant 100 or any of the spinal implants described herein. The spinal implant 200 can include an upper surface 202, a lower surface 204, two side surfaces 206, 208, a front surface 210, a back surface 212, an opening 214, one or more features 216, 218, and a solid body 220. The opening 214 can be oblong. The longest axis of the opening 214 can be between the side surfaces 206, 208. The opening 214 can include a smaller length than the opening 114. In some embodiments, the opening 214 for graft is located at the most posterior aspect of the spinal implant 100. This allows the graft to be in contact with the narrowest point in the disc. This is located at the point where the vertebral endplates can be easily viewed and decorticated.

The spinal implant 200 can be sized 1-2 cm longer than typical cage so that the opening 214 can be located at the periphery of the disc space. In FIGS. 4A and 4B, the spinal implant 100 has a greater overall length, e.g., the spinal implant 100 is extra-long compared with the implant 200. In some embodiments, the spinal implant 100 can be utilized for lateral insertions and the spinal implant 200 can be utilized for posterior or anterior insertions. Other methods of use are contemplated.

Figure 7A:
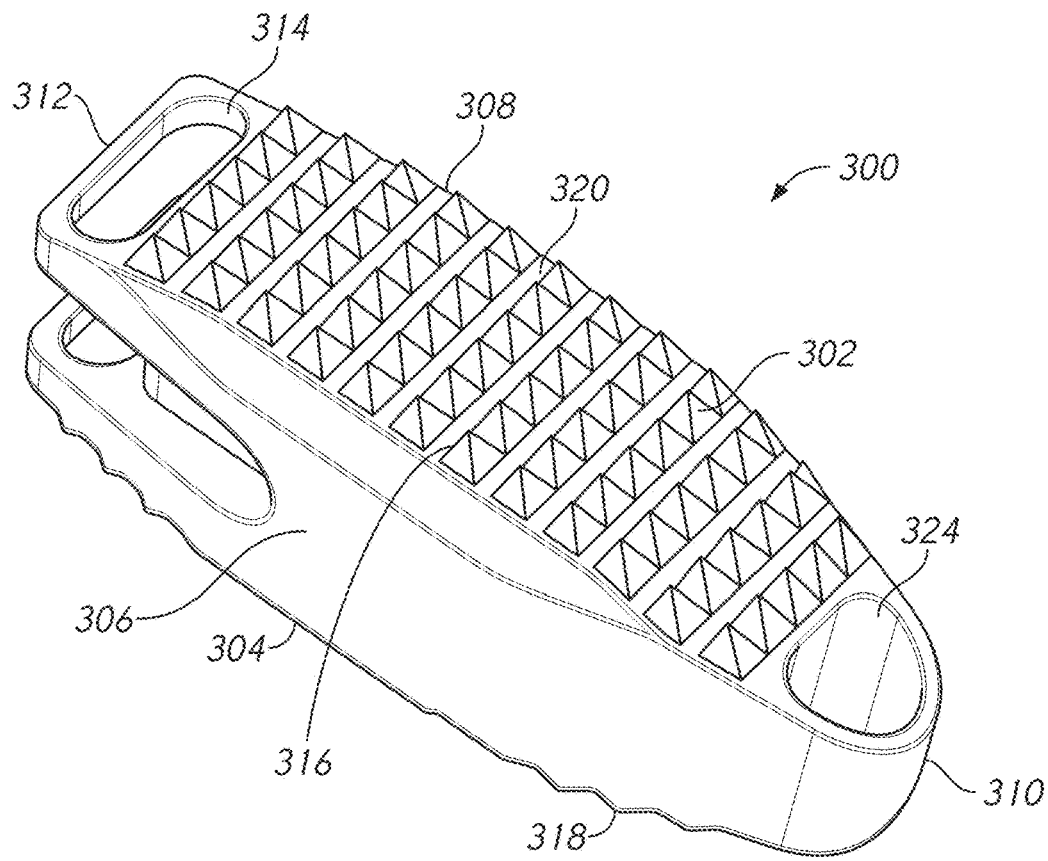
FIGS. 7A and 7B are schematic views of an embodiment of a spinal implant.
Figure 7B:
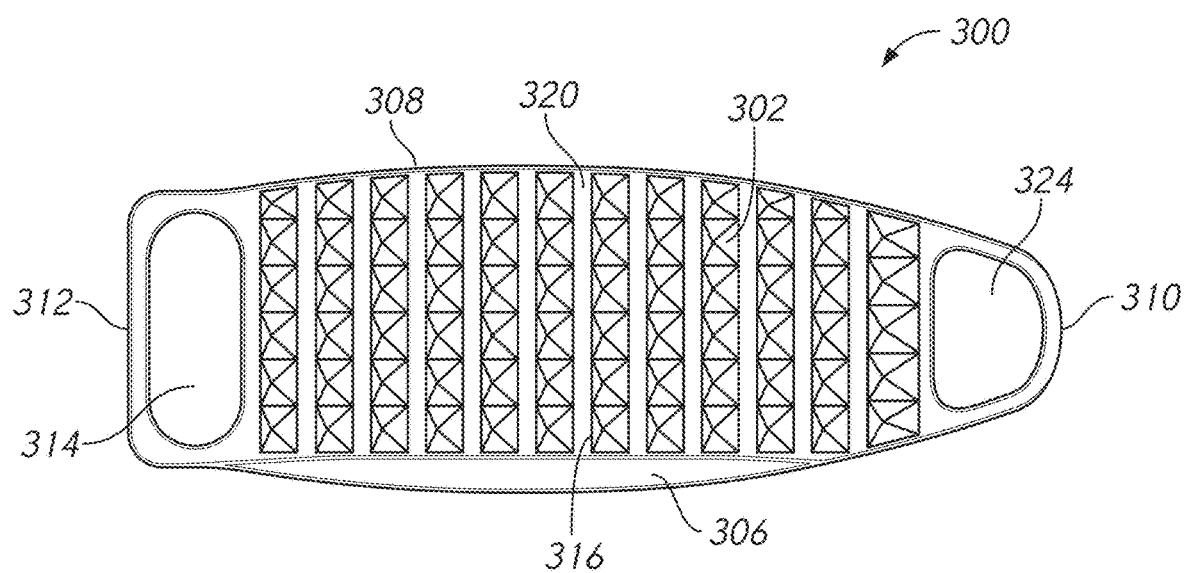

FIGS. 7A and 7B are schematic views of an embodiment of a spinal implant 300. The spinal implant 300 can include any of the features of the spinal implant 100 or any of the spinal implants described herein. The spinal implant 300 can include an upper surface 302, a lower surface 304, two side surfaces 306, 308, a front surface 310, a back surface 312, an opening 314, one or more features 316, 318, and a solid body 320. The opening 314 can be oblong. The longest axis of the opening 314 can be between the side surfaces 306, 308. In some methods of use, the opening 314 for graft can be located at the cortical rim. In some methods of use, the opening 314 for graft can be located at the back or posterior end of the implant for positioning near the cortical rim. The spinal implant 300 can include a second opening 324. In some methods of use, the opening 324 for graft can be located at the front or anterior end of the implant. In some methods of insertion, the opening 324 is also positioned near the cortical rim. The spinal implant 300 can be constructed similar to the spinal implant 100, 200, but with an opening at each of the two far end portions of the spinal implant 100. The openings 314, 324 can be located at opposite ends of the spinal implant 300. In some embodiments, one opening is posterior and one opening is anterior.

The second opening 324 can extend between the upper surfaces 302 and lower surface 304, or a portion thereof. The second opening 324 can extend between the vertebrae when the spinal implant 300 is inserted between adjacent vertebrae. The second opening 324 can extend generally vertically within the patient when the spinal implant 100 is inserted between adjacent vertebrae. In some embodiments, the second opening 324 is adjacent to the front surface 310. In some embodiments, the second opening 324 is adjacent to a portion of the two side surfaces 306, 308. In some embodiments, the second opening 324 is enclosed. The second opening 324 can be enclosed by the front surface 310 and at least a portion of the two side surfaces 306, 308. The second opening 324 can be tapered. The second opening 324 can narrow toward the front of the spinal implant 100. In some embodiments, the openings 314, 324 can have the same shape. In some embodiments, the openings 314, 324 can have a different shape. In some embodiments, the opening 314 has a longer length than the second opening 324. In some embodiments, the second opening 324 has a longer length than the opening 314. In some embodiments, the opening 314 has a larger surface area than the second opening 324. In some embodiments, the second opening 324 has a larger surface area than the opening 314.

Figure 8A:
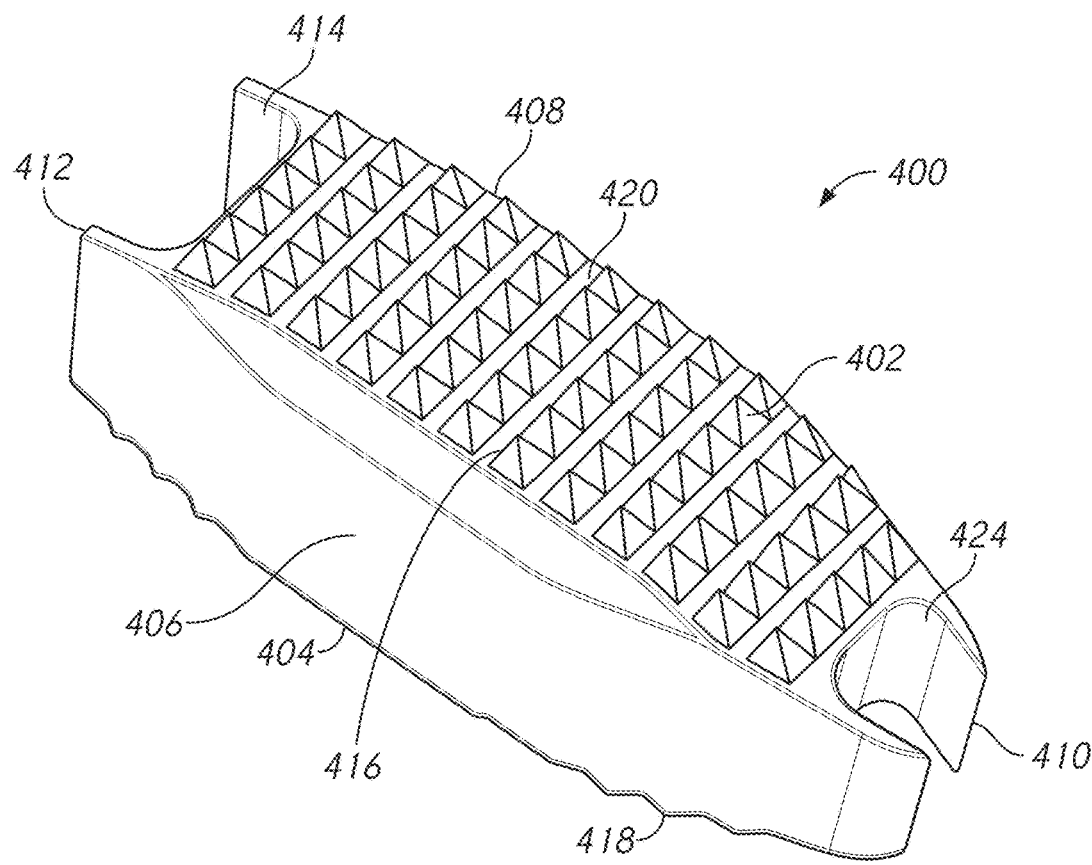
FIGS. 8A and 8B are schematic views of an embodiment of a spinal implant.
Figure 8B:
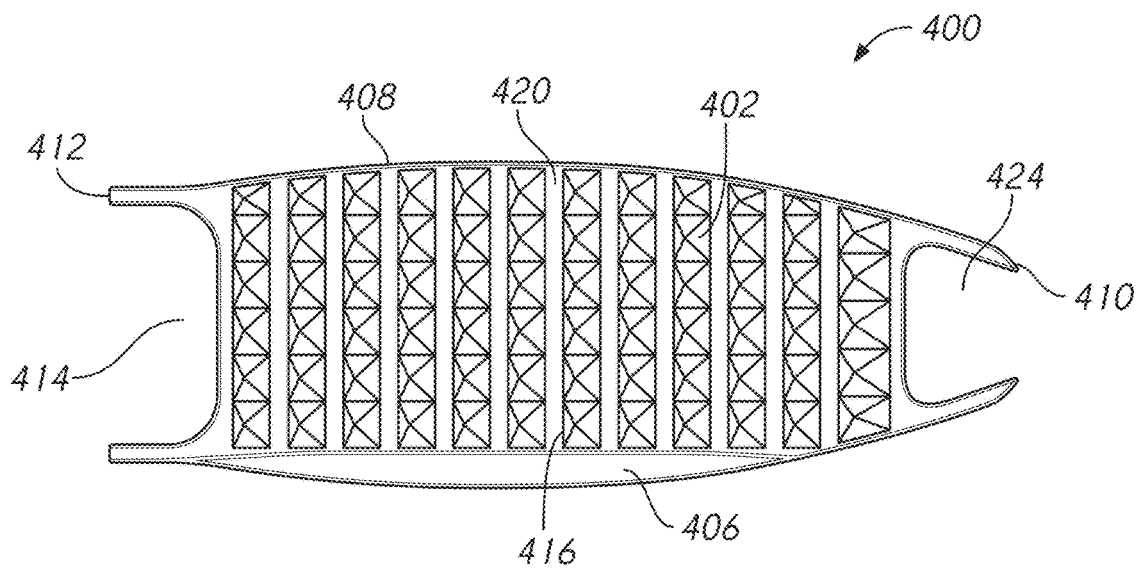

FIGS. 8A and 8B are schematic views of an embodiment of a spinal implant 400. The spinal implant 400 can include any of the features of the spinal implant 100 or any of the spinal implants described herein. The spinal implant 400 can include an upper surface 402, a lower surface 404, two side surfaces 406, 408, a front surface 410, a back surface 412, an opening 414, one or more features 416, 418, a solid body 420, and a second opening 424.

In some embodiments, the opening 414 is not enclosed. The opening 414 is only partially enclosed by the side surfaces 406, 408 and/or the back surface 412. In some embodiments, the back surface 412 is fully or partially removed. In some embodiments, the second opening 424 is not enclosed. The second opening 424 is only partially enclosed by the side surfaces 406, 408 and/or the front surface 410. In some embodiments, the front surface 410 is fully or partially removed.

In some embodiments, most of the front surface 410 and the back surface 412 is removed. The spinal implant 400 can be constructed similar to the spinal implant 300, but with at least one of the far end portions of the spinal implant 400 partially removed. The spinal implant 400 can form open pockets into which the graft is deposited, instead of having the graft fully contained within the spinal implant 400. Thus, more bone graft material can be packed into the opening 414 and/or opening 424. The graft can be packed closest to the entry point of the disc space. The bone graft is placed in an open pocket rather than contained within the spinal implant 400. The open pocket design can allow for packing of more bone graft into the pocket or opening 414 that ends up closest to the disc entry point.

Figure 9A:
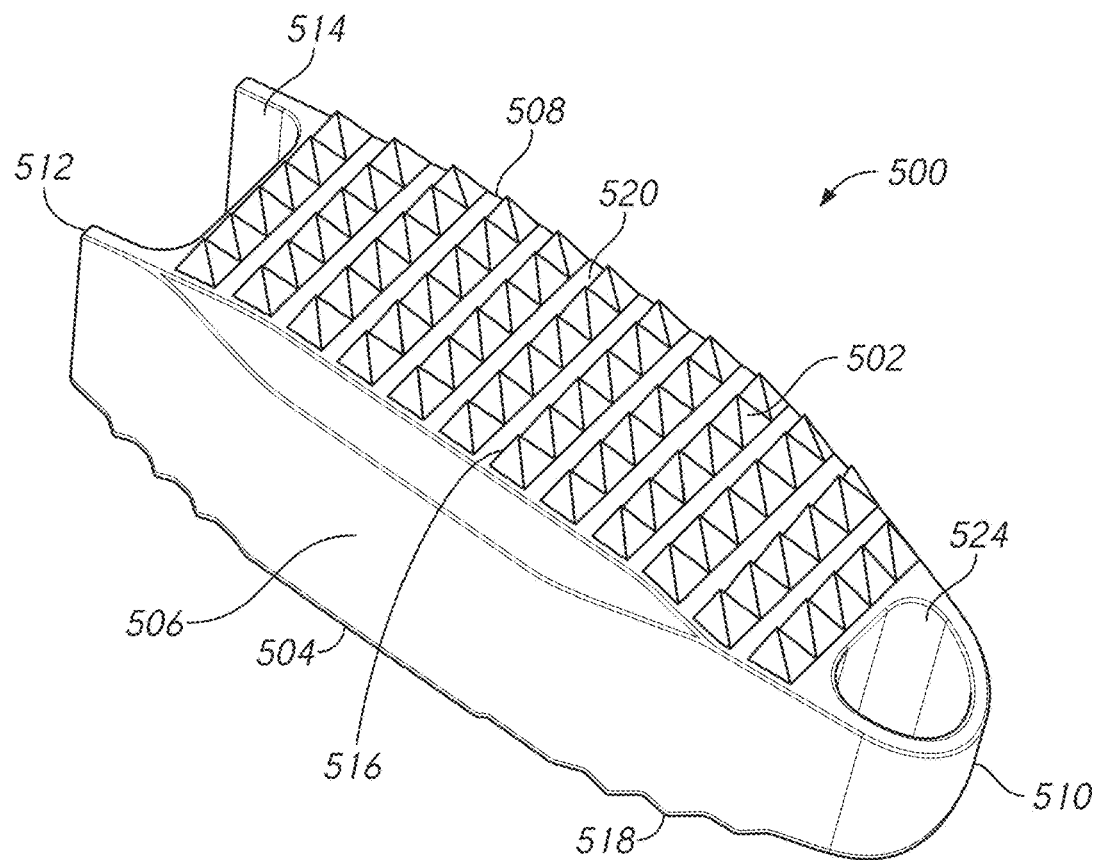
FIGS. 9A and 9B are schematic views of an embodiment of a spinal implant.
Figure 9B:
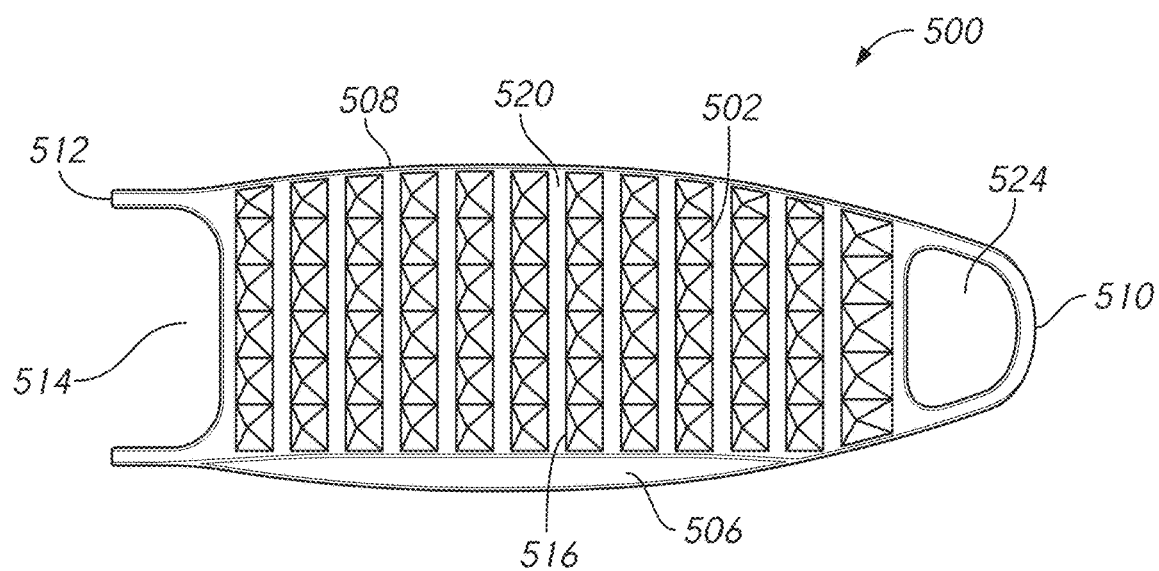

FIGS. 9A and 9B are schematic views of an embodiment of a spinal implant 500. The spinal implant 500 can include any of the features of the spinal implant 100 or any of the spinal implants described herein. The spinal implant 500 can include an upper surface 502, a lower surface 504, two side surfaces 506, 508, a front surface 510, a back surface 512, an opening 514, one or more features 516, 518, a solid body 520, and a second opening 524.

The spinal implant 500 can be constructed similar to the spinal implant 300, 400. The spinal implant 500 can include one enclosed opening and one partially enclosed opening or pocket. In the illustrated embodiment, the second opening 524 is enclosed and the opening 514 is partially enclosed. The opening 514 is only partially enclosed by the side surfaces 406, 408 and/or the back surface 512. In some embodiments, the back surface 512 is fully or partially removed. In some embodiments, not illustrated, the opening 514 is enclosed and the second opening 524 is partially enclosed. The spinal implant 500 can include one far end portion of the spinal implant 500 forming the second opening 524, and the other far end portion of the spinal implant 500 forms the opening 514. In some embodiments, at least one opening 514, 524 is designed to contain bone graft. In some embodiments, the enclosed opening contains bone graft. In some embodiments, the partially enclosed opening contains bone graft. In some embodiments, the second opening 524 located near the front of the spinal implant 500 is contained or enclosed. In some embodiments, the opening 514 located near the back of the spinal implant 500 is open or partially enclosed, forming a pocket.

Figure 10A:
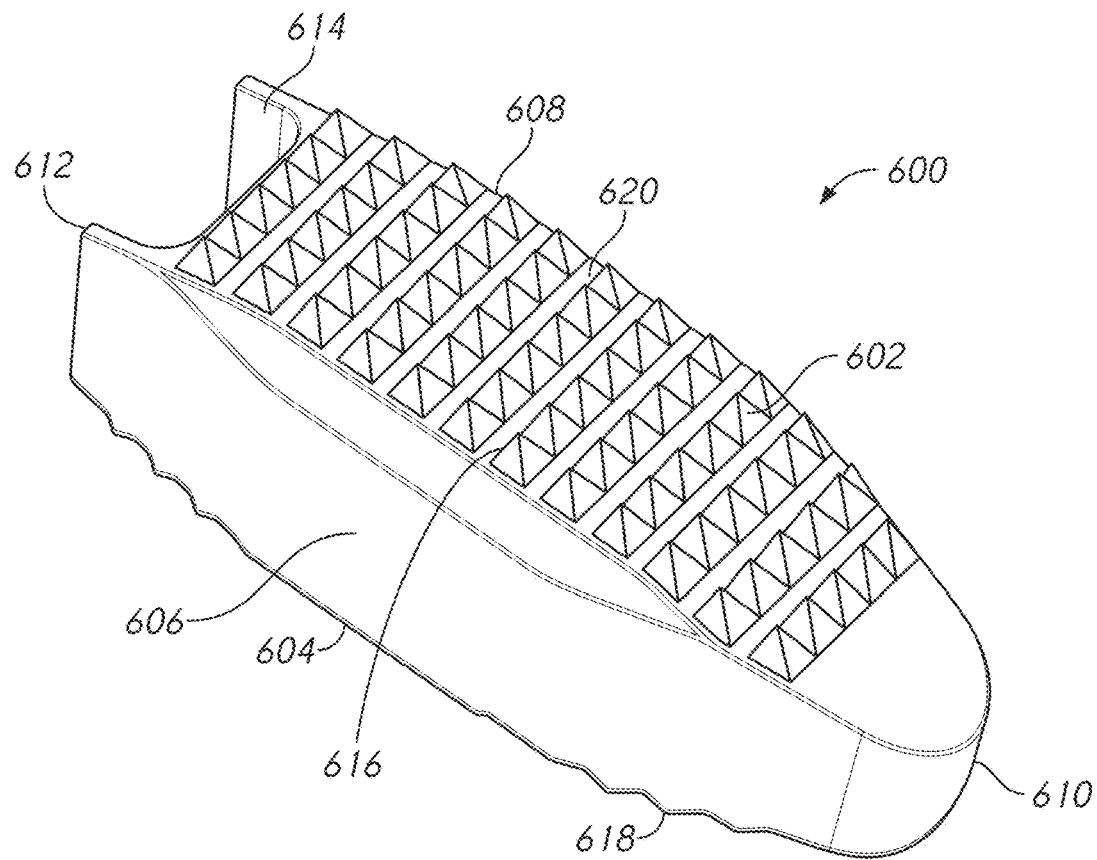
FIGS. 10A and 10B are schematic views of an embodiment of a spinal implant.
Figure 10B:
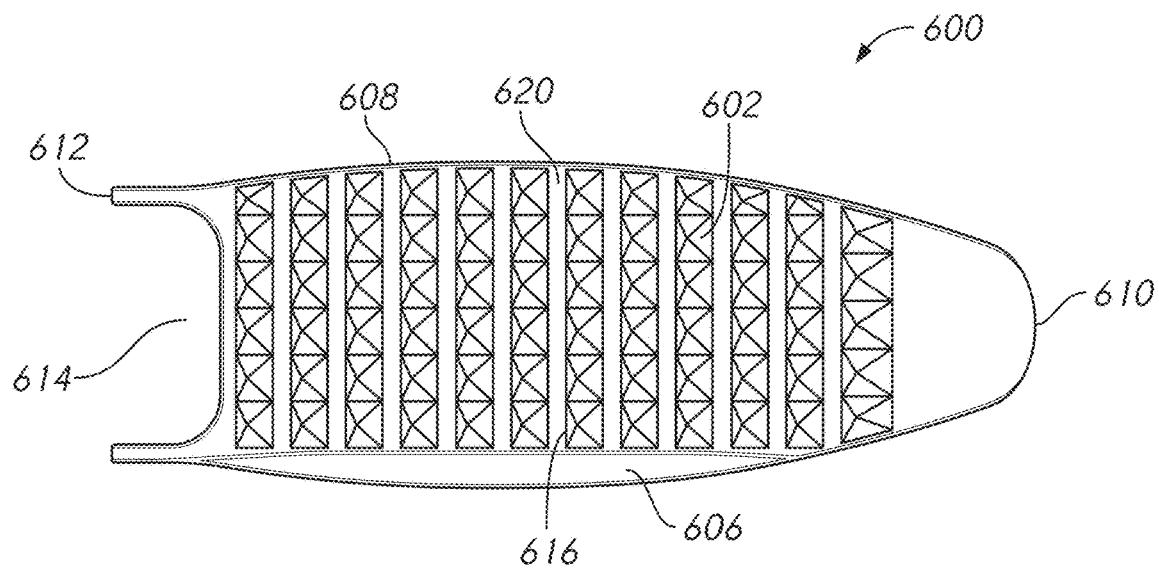
Figure 11A:
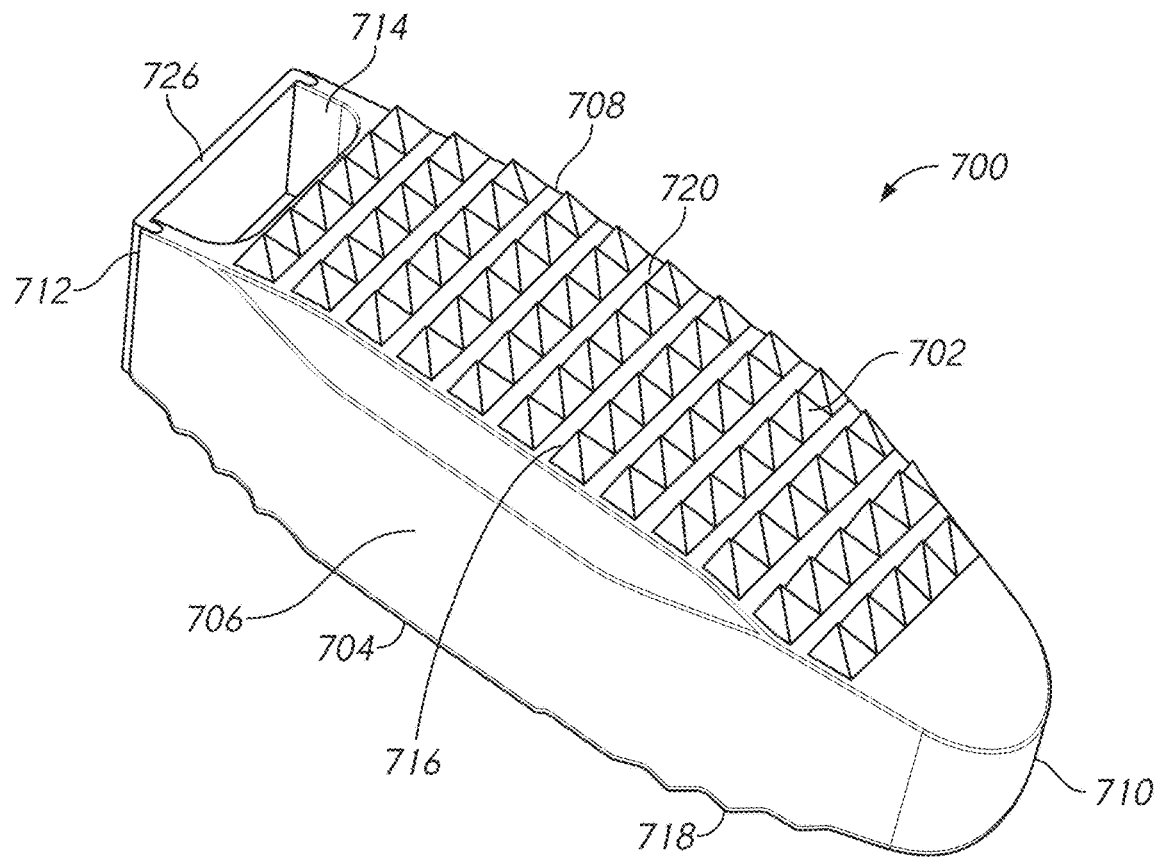
FIGS. 11A and 11B are schematic views of an embodiment of a spinal implant.
Figure 11B:
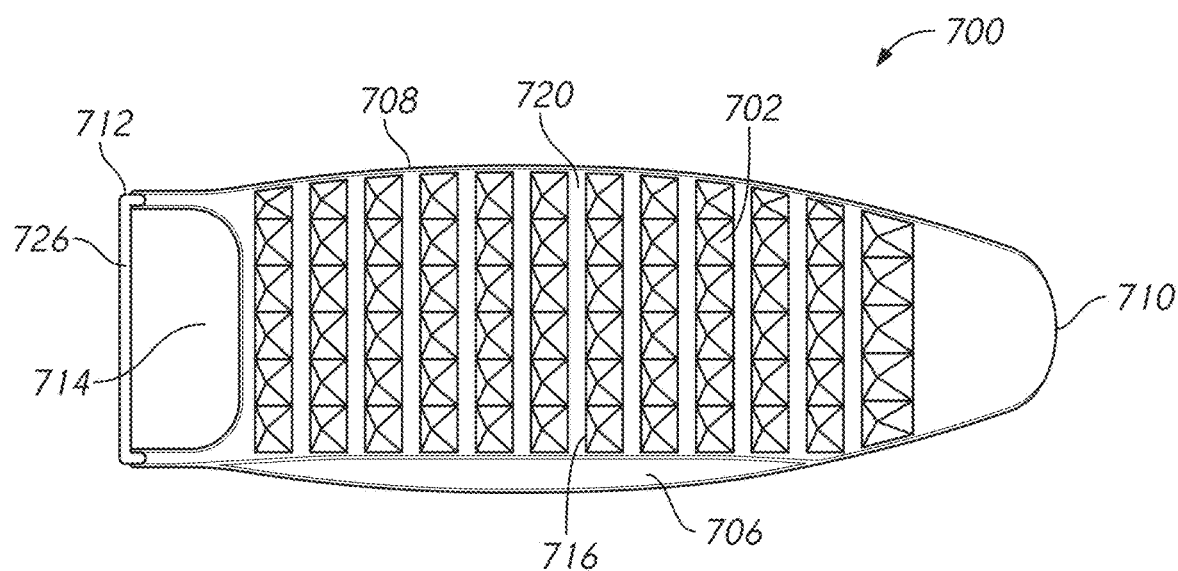

FIGS. 10A and 10B are schematic views of an embodiment of a spinal implant 600. The spinal implant 600 can include any of the features of the spinal implant 100 or any of the spinal implants described herein. The spinal implant 600 can include an upper surface 602, a lower surface 604, two side surfaces 606, 608, a front surface 610, a back surface 612, an opening 614, one or more features 616, 618, and a solid body 620. The spinal implant 600 can include a partially enclosed opening 614. In some embodiments, the opening 614 is not enclosed. The opening 614 is only partially enclosed by the side surfaces 606, 608 and/or the back surface 612. In some embodiments, the back surface 612 is fully or partially removed. The spinal implant 600 can include one open pocket located at a far end portion of the spinal implant 600 for depositing bone graft material. Bone graft material can be packed into the pocket after the spinal implant 600 is inserted in the disc space. The spinal implant 600 can include only one area for bone graft, located as the posterior aspect of the spinal implant 600. The opening 614 can be a pocket for the graft. In some methods, the graft can be packed into the pocket 614 before the spinal implant 600 has been inserted. In some methods, the graft can be packed into the pocket 614 after the spinal implant 600 has been inserted FIGS. 11A and 11B are schematic views of an embodiment of a spinal implant 700. The spinal implant 700 can include any of the features of the spinal implant 100 or any of the spinal implants described herein. The spinal implant 700 can include an upper surface 702, a lower surface 704, two side surfaces 706, 708, a front surface 710, a back surface 712, an opening 714, one or more features 716, 718, and a solid body 720. The spinal implant 700 can include a partially enclosed opening 714. The opening 714 is only partially enclosed by the side surfaces 706, 708.

The spinal implant 700 can include a cap 726. The cap 726 can be removable to allow for insertion of the bone graft into the opening 714. The cap 726 can form the back surface 712 of the spinal implant 700 when coupled to the spinal implant 700. The spinal implant 700 can include the opening 714 located at a far end portion of the cage for depositing bone graft material. Bone graft material can be packed into the opening 714 before or after the spinal implant 700 is inserted in the disc space. In some methods of use, the cap 726 can be coupled to the two side surfaces 706, 708 after bone graft material is packed into the opening 714. In some methods of use, the cap 726 can be coupled to the two side surfaces 706, 708 before the spinal implant 700 is inserted in the disc space. In some methods of use, the cap 726 can be coupled to the two side surfaces 706, 708 after the spinal implant 700 is inserted in the disc space.

The cap 726 can be coupled to the two side surfaces 706, 708 by various mechanical connections including a pivot, snap fit, frictional fit, a threaded connection, a bayonet connection, a tongue and groove, a dovetail, or an adhesive. In some embodiments, the cap 726 can be designed to couple to the two side surfaces 706, 708. In some embodiments, the cap 726 can be fixed to at least one of the two side surfaces 706, 708. Other connections are contemplated. The spinal implant 700 can be constructed similar to the spinal implant 600 except that the cap 726 can be attached to the spinal implant 700 to enclose the back surface 712. The cap 726 can function to enclose the graft material. The cap 726 can be designed to prevent or reduce the likelihood that the graft can migrate out and away from the spinal implant 700 after surgery is completed.

In some methods of use, the bone graft is inserted in the spinal implant 700 outside of the body of the patient. In some methods of use, the bone graft is inserted into the opening 714. In some methods of use, the bone graft is enclosed by the cap 726. In some methods of use, the cap 726 is secured outside of the body of the patient. In some methods of use, the solid body 720, the graft material, and the cap 726 are inserted as a unit into the body of the patient. The spinal implant 700 is inserted until the graft material within the opening 714 is positioned to span the cortical rim.

In some methods of use, the bone graft is inserted in the spinal implant 700 inside the body of the patient. In some methods of use, the solid body 720 is positioned between adjacent vertebrae. In some methods of use, the bone graft is inserted into the opening 714 to align the graft with the cortical rim. The position of the bone graft can be verified before securing the cap 726. In some methods of use, the bone graft is enclosed by the cap 726 within the body of the patient. In some methods, the solid body 720 is inserted into the patient. The bone graft can be inserted before or after the solid body 720 is inserted. In some methods, the cap 726 can be secured outside of the body of the patient. In some methods, the cap 726 is secured in the body after the solid body 720 and graft are positioned.

Figure 12A:
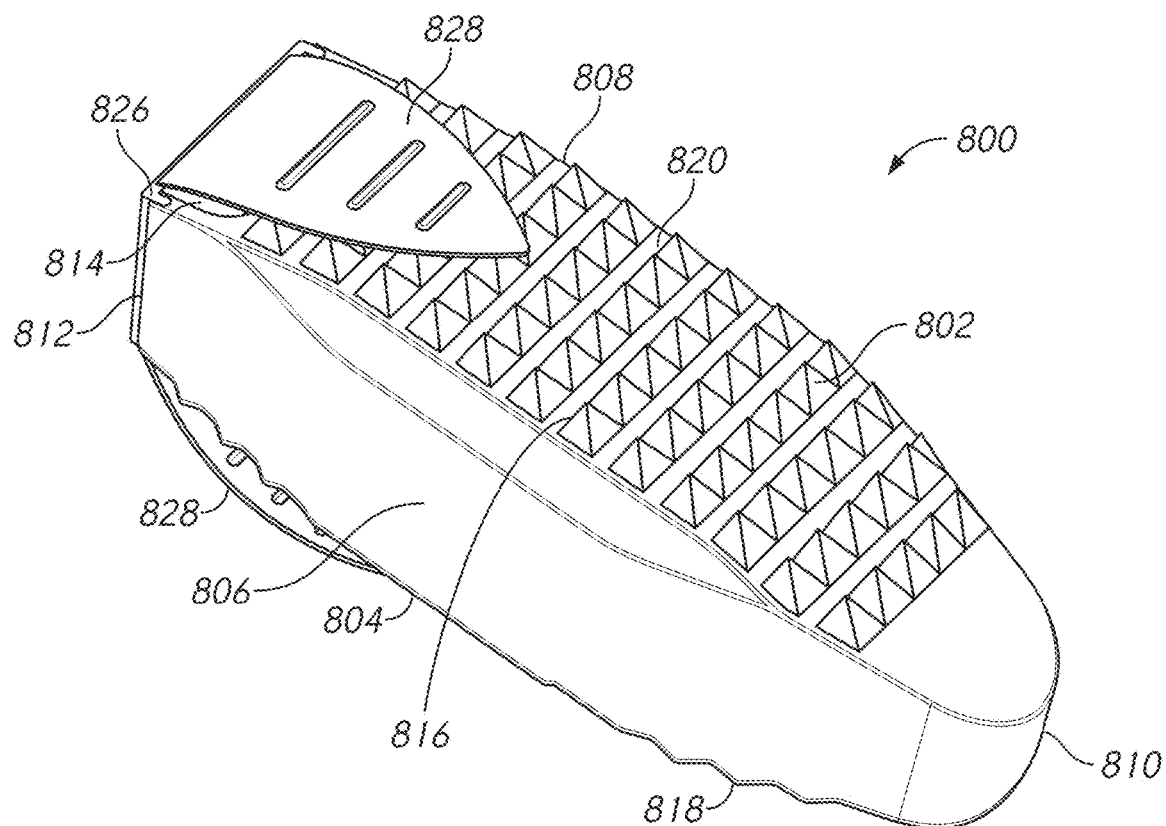
FIGS. 12A and 12B are schematic views of an embodiment of a spinal implant.
Figure 12B:
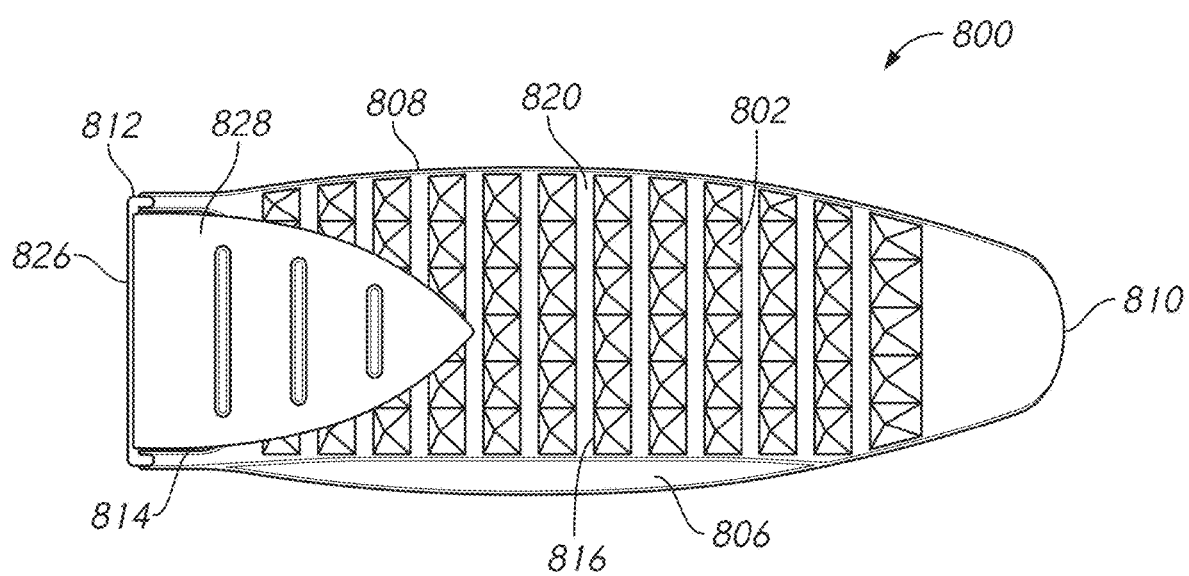

FIGS. 12A and 12B are schematic views of an embodiment of a spinal implant 800. The spinal implant 800 can include any of the features of the spinal implant 100 or any of the spinal implants described herein. The spinal implant 800 can include an upper surface 802, a lower surface 804, two side surfaces 806, 808, a front surface 810, a back surface 812, an opening 814, one or more features 816, 818, a solid body 820, and a cap 826. The spinal implant 800 can include a partially enclosed opening 814. The opening 814 can be partially enclosed by the side surfaces 806, 808. The cap 826 can be removable to allow for insertion of the bone graft into the opening 814. The cap 826 can be coupled to the two side surfaces 806, 808. The cap 826 can form the back surface 812 of the spinal implant 800 when the cap 826 is coupled to the spinal implant 800.

The spinal implant 800 can include one or more blades 828. The illustrated embodiment includes two blades 828 but other configurations are contemplated (e.g., one blade, two blades, three blades, four blades, five blades, six blades, etc.). The blade tip can extend at least one centimeter away from the spinal implant 800 (e.g., one centimeter, two centimeters, between one and two centimeters, etc.). The one or more blades 828 can extend through the cap 826. The one or more blades 828 can extend through other portions of the spinal implant 800, such as the opening 814. In the illustrated embodiment, one blade 828 extends upward through the upper vertebral bone and one blade 828 extends downward through the lower vertebral bone. The one or more blades 828 can be coupled to the cap 826. The one or more blades 828 can be integrally formed with the cap 826. The one or more blades 828 can include a blade tip designed to penetrate bone. Each blade 828 can include a barb to facilitate engagement with the bone.

In some methods, the solid body 820 is inserted into the patient. The bone graft can be inserted before or after the solid body 820 is inserted. In some methods, the cap 826 can be secured outside of the body of the patient. In some methods, the cap 826 is secured in the body after the solid body 820 and graft are positioned in the body. In some methods, the one or more blades 828 are secured to the cap 826 outside of the body of the patient. In some methods, the one or more blades 828 are secured to the cap 826 inside of the body of the patient. In some methods, the one or more blades 828 are inserted into the body of the patient and through the cap 826. In some methods, the one or more blades 828 are driven into the vertebral bone after positioning the spinal implant 800.

The spinal implant 800 can be constructed similar to the spinal implant 700, except the cap 826 has one or more blades 828 with associated barbs configured to penetrate the vertebral bones above and below the spinal implant 800. The blades 828 can be designed to secure the spinal implant 800 to the vertebral bone after the spinal implant 800 is inserted in the disc space. The cap 826 thus becomes anchored to the bones. There can be two blades 828 as shown, or only one blade 828. The blades 828 can reduce the risk of the spinal implant 800 from backing out of the disc space. The blades 828 can perform various functions. The blades 828 can hold the cap 826 in place. The blades 828 can hold the bone graft in place. The blades 828 can prevent the spinal implant 800 from backing out. The blades 828 can stabilize the spine.

Figure 13A:
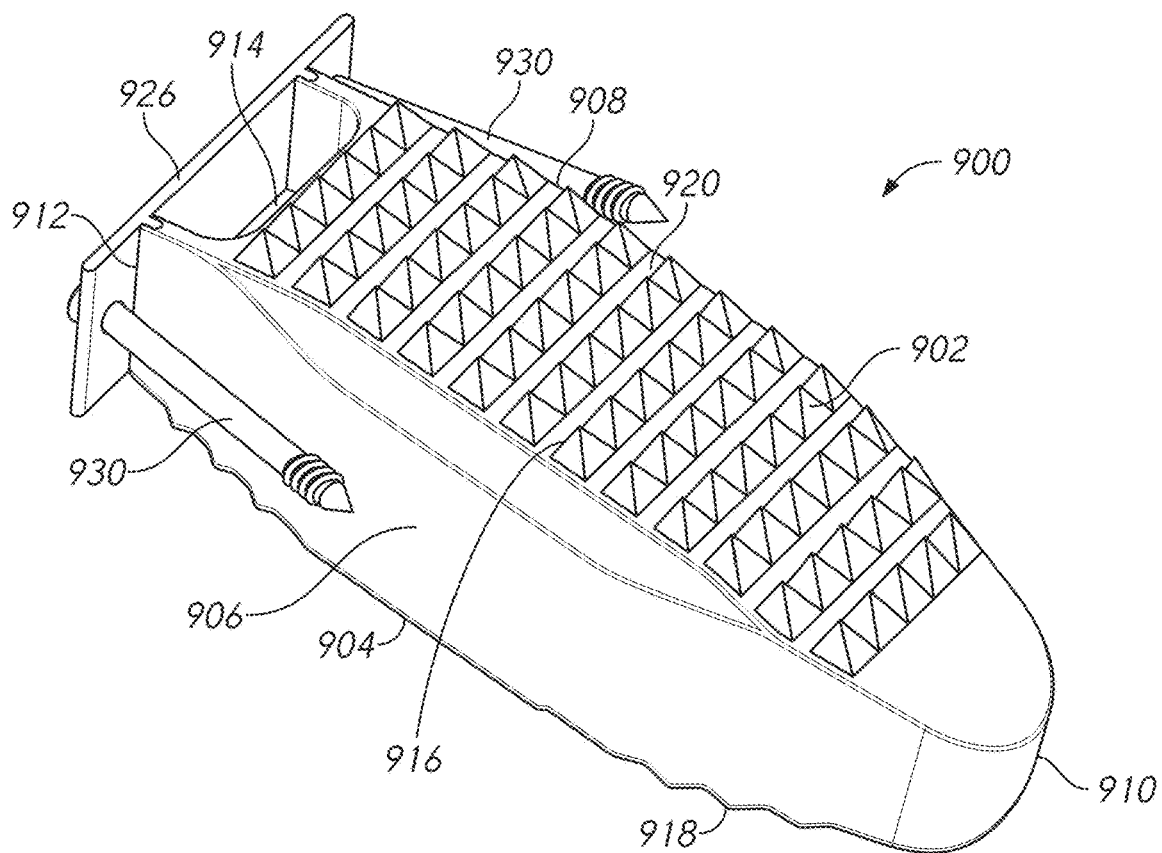
FIGS. 13A and 13B are schematic views of an embodiment of a spinal implant.
Figure 13B:
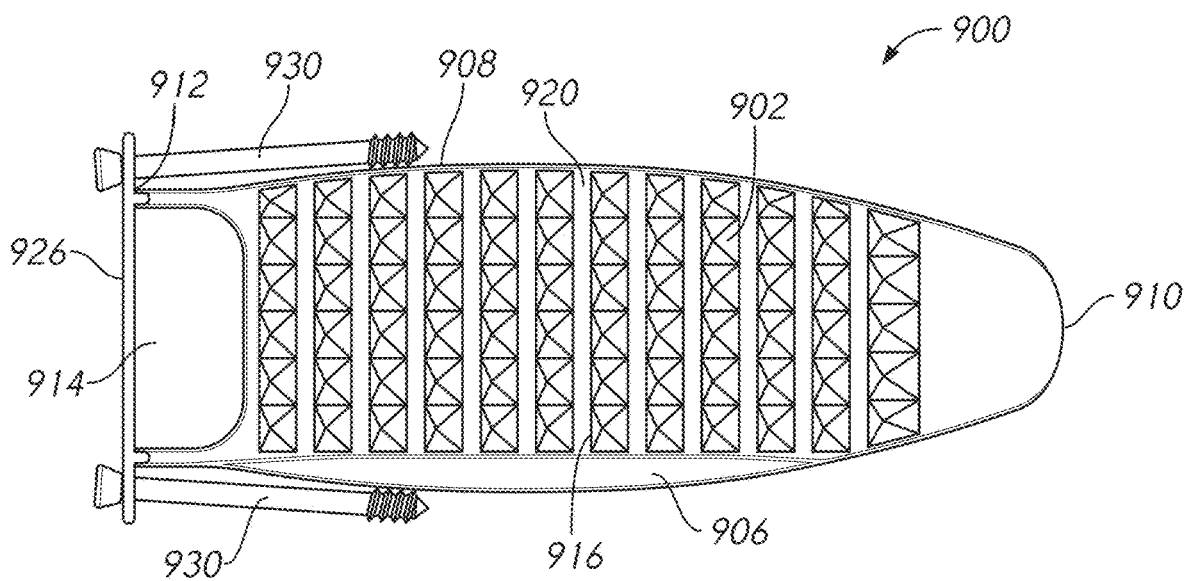

FIGS. 13A and 13B are schematic views of an embodiment of a spinal implant 900. The spinal implant 900 can include any of the features of the spinal implant 100 or any of the spinal implants described herein. The spinal implant 900 can include an upper surface 902, a lower surface 904, two side surfaces 906, 908, a front surface 910, a back surface 912, an opening 914, one or more features 916, 918, a solid body 920, and a cap 926. The spinal implant 800 can include a partially enclosed opening 914. The opening 914 is only partially enclosed by the side surfaces 906, 908. The cap 926 can be removable to allow for insertion of the bone graft into the opening 914. The cap 926 can be coupled to the two side surfaces 906, 908. The cap 926 can form the back surface 912 of the spinal implant 900.

The spinal implant 900 can include one or more fixation devices 930. The illustrated embodiment includes two fixation devices 930 but other configurations are contemplated (e.g., one fixation device, two fixation devices, three fixation devices, four fixation devices, five fixation devices, or six fixation devices, etc.). In the illustrated embodiment, the fixation devices 930 are bone screws, but other fixation devices are contemplated (e.g., sutures, plugs, pins, or spikes, etc.). The fixation devices 930 can extend at least one centimeter away from the sides surfaces 906, 908 spinal implant 900 (e.g., one centimeter, two centimeters, between one and two centimeters, etc.). The fixation devices 930 can extend through the cap 926.

In some methods, the solid body 920 is inserted into the patient. The bone graft can be inserted before or after the solid body 920 is inserted. In some methods, the cap 926 can be secured outside or inside of the body of the patient. In some methods, the one or more fixation devices 930 are driven through the vertebral bone inside of the body of the patient. In some methods, the one or more fixation devices 930 are driven through the vertebral bone after positioning the solid body 920 and the bone graft within the intervertebral space.

The fixation devices 930 can extend away from the spinal implant 900. In the illustrated embodiment, one fixation device 930 extends upward through the upper vertebral bone and fixation device 930 extends downward through the lower vertebral bone. The fixation devices 930 can be coupled to the cap 926. The fixation devices 930 can include a tip designed to penetrate bone. The cap 926 thus becomes anchored to the bones. There can be two fixation devices 930 as shown, or only one fixation device 930. The fixation devices 930 can reduce the risk of the spinal implant 900 from backing out of the disc space. The fixation devices 930 can perform various functions. The fixation devices 930 can hold the cap 926 in place. The fixation devices 930 can hold the bone graft in place. The fixation devices 930 can prevent the spinal implant 900 from backing out. The fixation devices 930 can stabilize the spine.

In some embodiments, the fixation devices 930 can extend through the center of the cap 926. In some embodiments, the cap 926 can be extended along the width of the spinal implant 900. In some embodiments, the fixation devices 930 do not enter the opening 914 which is designed to contain bone graft. In some embodiments, the fixation devices 930 extend at least partially through the opening 914 which is designed to contain bone graft. The fixation devices 930 can be in line with the spinal implant 900. The fixation devices 930 can extend up and down. The fixation devices 930 can be divergent away and outward as illustrated in FIG. 13B. The fixation devices 930 can be divergent away and inward.

The spinal implant 900 can be constructed similarly to the spinal implant 800, except the cap 926 has associated fixation devices 930 instead of blades 828. The fixation devices 930 can be metal screws. The advantage of this construction is that the fixation devices 930 can be passed through extended sides of the cap 926 so that the fixation devices 930 do not violate the region of the pocket or opening 914 that contains the graft. In some embodiments, the fixation devices 930 can function the same as the blades 828. In some embodiments, the fixation devices 930 pass through the mid portion of the cap 926 and do not diverge away from the spinal implant 900. In such a case, some part of the fixation device 930 would be in the area of the graft, however. In some embodiments, the cap 926 extends past the two side surfaces 906, 908 as shown. In some embodiments, the cap 926 extends past at least one of the two side surfaces 906, 908. It is also possible to have the cap 926 extend only on one side of the spinal implant 900. In some embodiments, the cap 926 supports a single fixation device 930. In some embodiments, the cap 926 supports two or more fixation device 930. In some embodiments, the cap 926 supports two or more fixation device 930 on either side of the spinal implant 900, such as near the side surface 906.

Figure 14A:
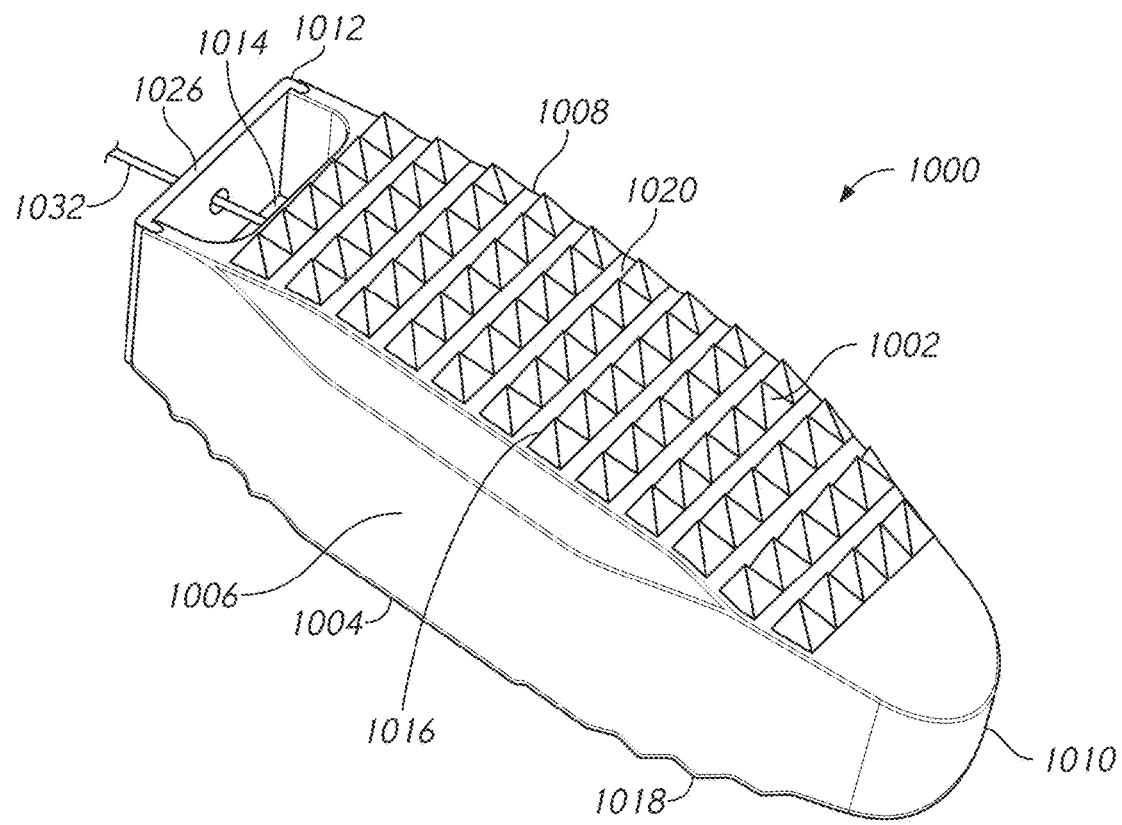
FIGS. 14A and 14B are schematic views of an embodiment of a spinal implant.
Figure 14B:
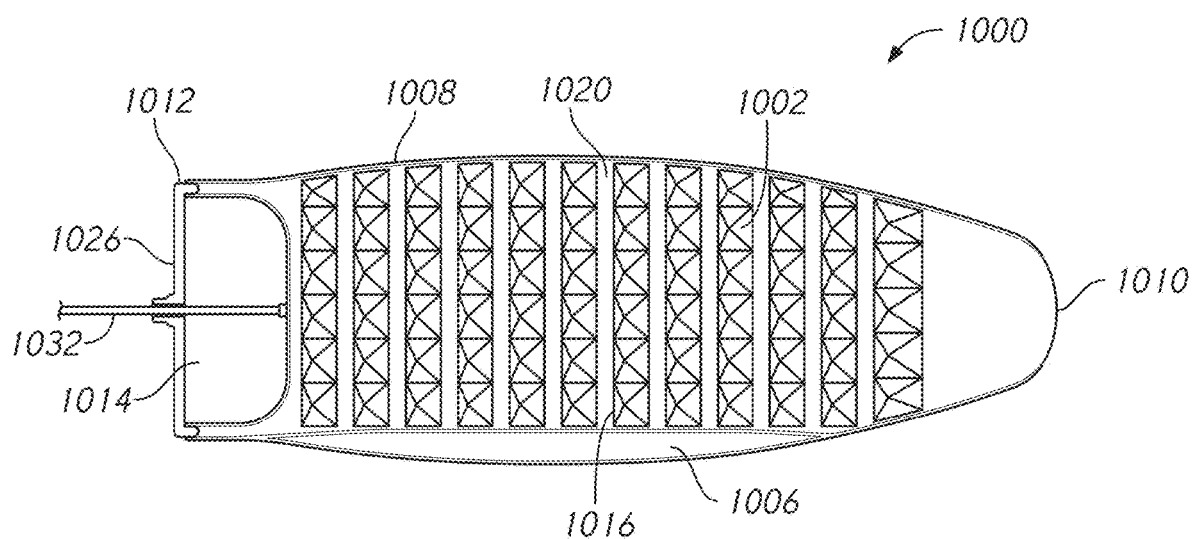

FIGS. 14A and 14B are schematic views of an embodiment of a spinal implant 1000. The spinal implant 1000 can include any of the features of the spinal implant 100 or any of the spinal implants described herein. The spinal implant 1000 can include an upper surface 1002, a lower surface 1004, two side surfaces 1006, 1008, a front surface 1010, a back surface 1012, an opening 1014, one or more features 1016, 1018, a solid body 1020, and a cap 1026. The spinal implant 1000 can include a partially enclosed opening 1014. The opening 1014 is only partially enclosed by the side surfaces 1006, 1008. The cap 1026 can be removable to allow for insertion of the bone graft into the opening 1014. The cap 1026 can be coupled to the two side surfaces 1006, 1008. The cap 1026 can form the back surface 1012 of the spinal implant 1000.

In some embodiments, a wire or cable 1032 is coupled at one end to the body of the spinal implant 1000. The cable 1032 can be fixed to an inside surface of the spinal implant 1000. The cable 1032 can be coupled inside the end pocket or opening 1014. After the spinal implant 1000 is inserted and bone graft material is packed in the opening 1014, the cap 1026 can be fed along the cable 1032. The cap 1026 can be guided down the cable 1032 to rest against the spinal implant 1000. The cap 1026 can be guided down the cable 1032 to rest against posterior vertebral bodies. In the rest position, a crimp or cinch 1034 can be formed to lock the cap 1026 to the cable 1032. In some methods, the cinch 1034 can be made with pliers. In some methods, excess wire can be cut away.

Figure 15A:
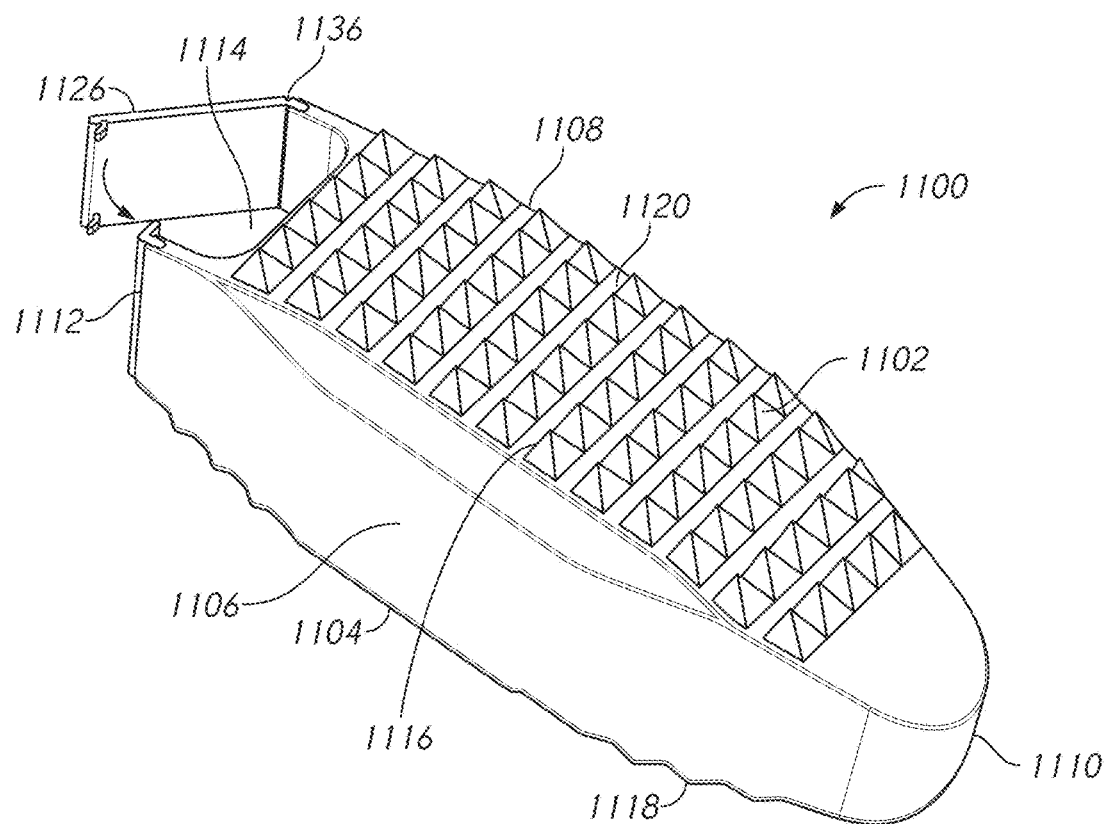
FIGS. 15A and 15B are schematic views of an embodiment of a spinal implant.
Figure 15B:
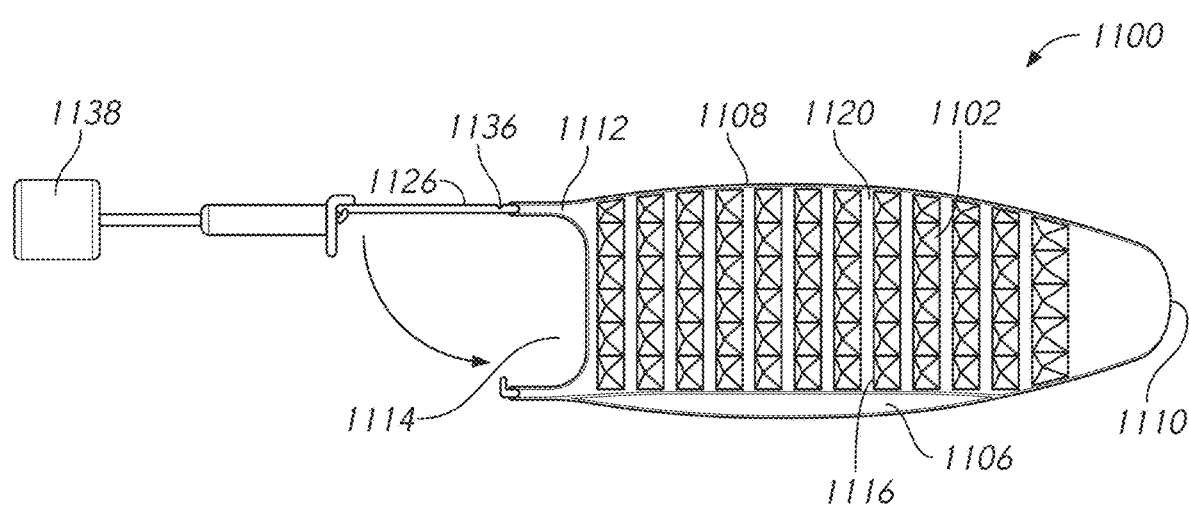
Figure 16A:
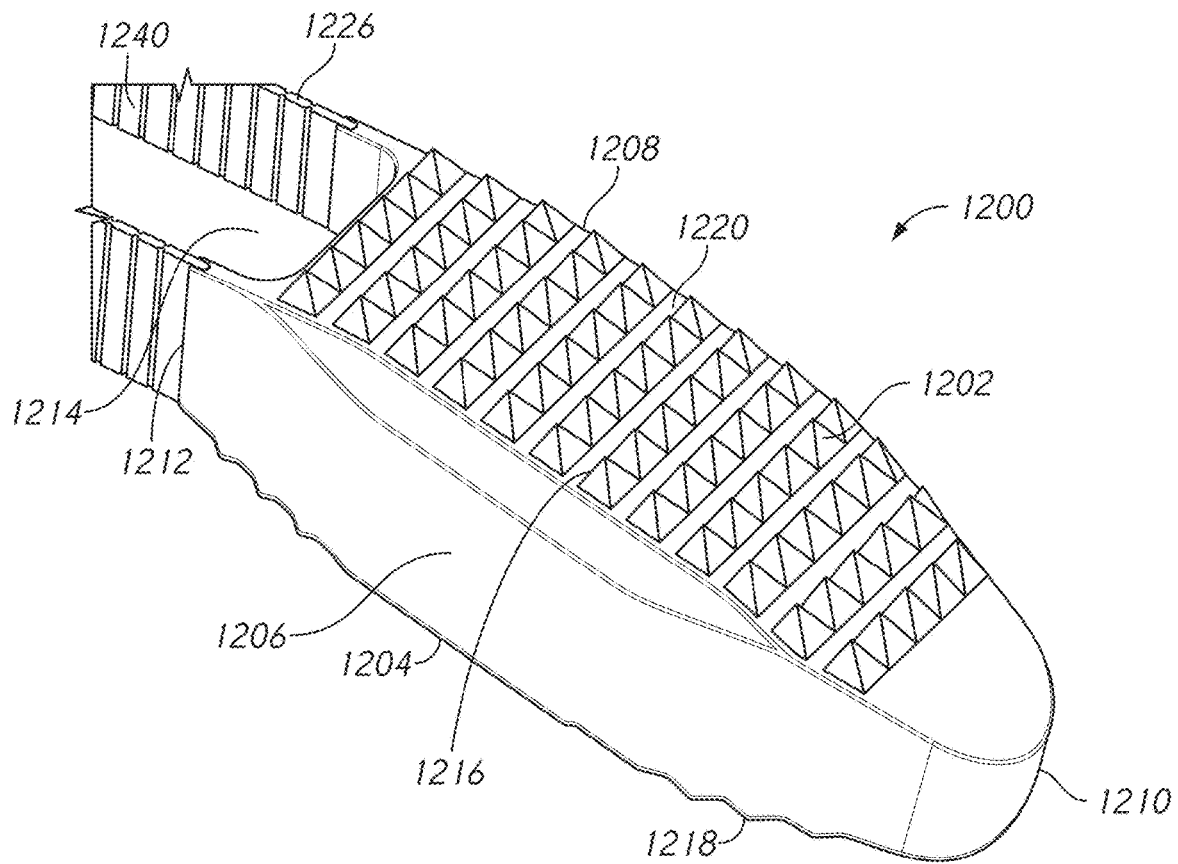
FIGS. 16A-16D are schematic views of an embodiment of a spinal implant.
Figure 16B:
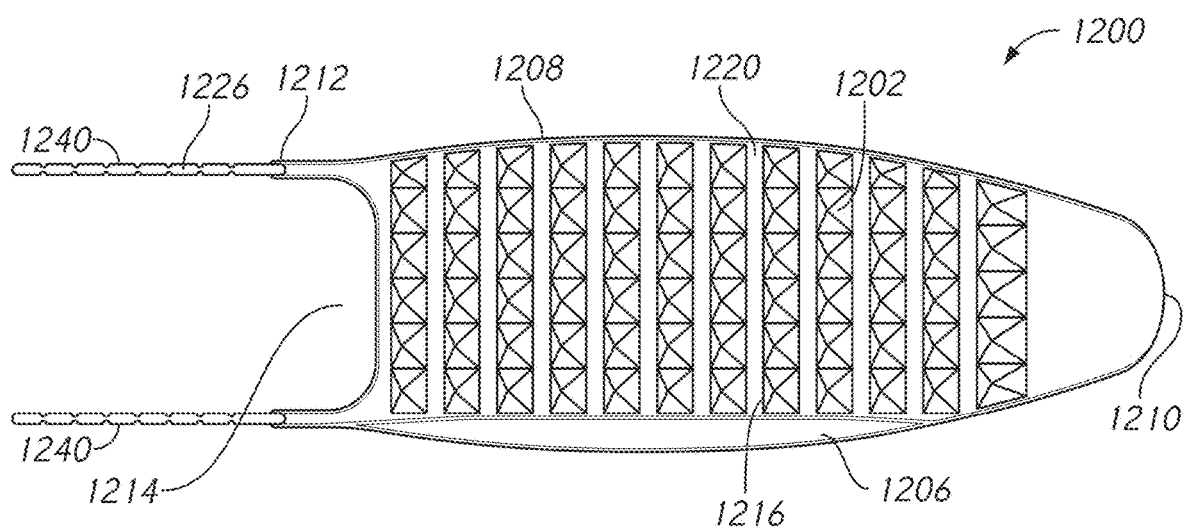
Figure 16C:
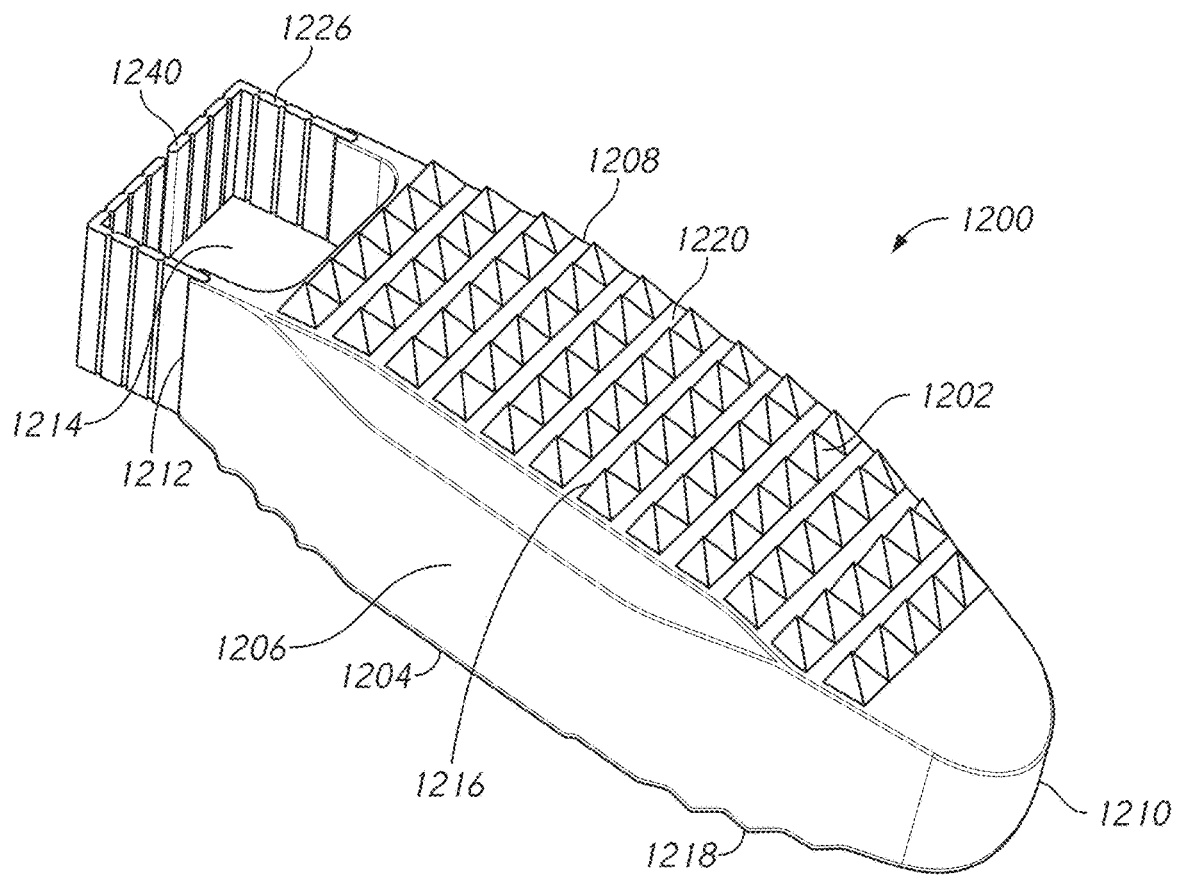
Figure 16D:
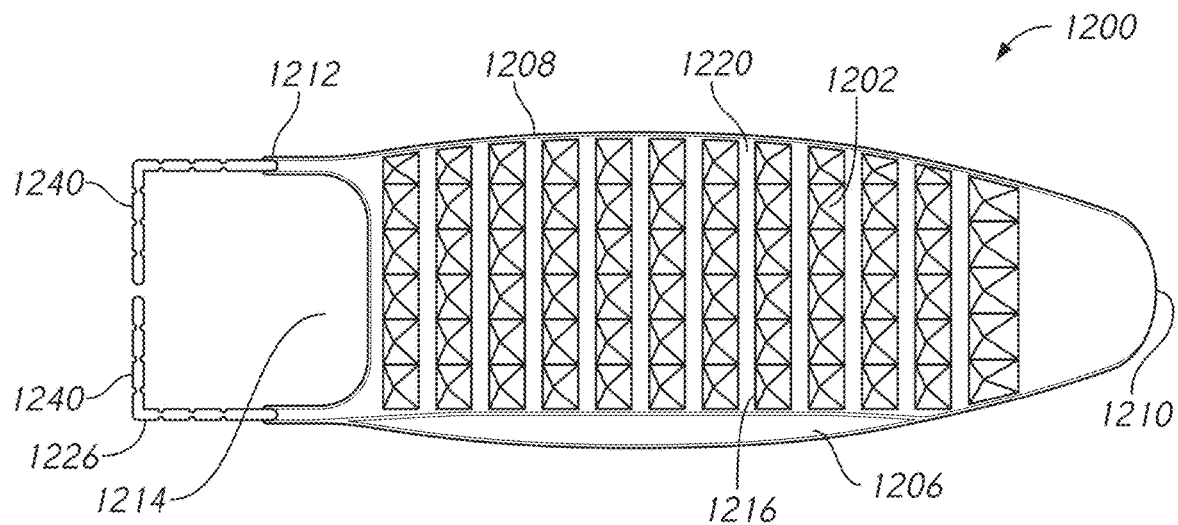

FIGS. 15A and 15B are schematic views of an embodiment of a spinal implant 1100. The spinal implant 1100 can include any of the features of the spinal implant 100 or any of the spinal implants described herein. The spinal implant 1100 can include an upper surface 1102, a lower surface 1104, two side surfaces 1106, 1108, a front surface 1110, a back surface 1112, an opening 1114, one or more features 1116, 1118, a solid body 1120, and a cap 1126. The spinal implant 1100 can include a partially enclosed opening 1114. The opening 1114 is only partially enclosed by the side surfaces 1106, 1108. The cap 1126 can be openable to allow for insertion of the bone graft into the opening 1114. The cap 1126 can be coupled to the two side surfaces 1106, 1108. The cap 1126 can form the back surface 1112 of the spinal implant 1100.

In some embodiments, the cap 1126 can be a malleable metal cap. The cap 1126 can be folded down to seal bone graft deposited in the open pocket or opening 1114. In some embodiments, a divot 1136 can be formed in the cap 1126 to allow for bending at the correct spot. In some embodiments, a pusher tool 1138 has a hooked end that provides the correct vector force to ensure the cap 1126 closes toward the pocket or opening 1114 in the spinal implant 1100. A barb 1140 can be formed on the edge of the cap 1126 to lock onto the side edge 1108 so that the closure is secure.

After insertion of the spinal implant 1100 into the disc space, the cap 1126 is folded down to lock bone graft in the opening 1114 and prevent migration of the bone graft out of the opening 1114. The cap 1126 can be secured in any manner described herein. In some embodiments, the edge of the cap 1126 can snap lock to at least one side surface 1106, 1108 of the spinal implant 1100. In some embodiments, a pusher tool 1138 is provided to facilitate the securement of the cap 1126. The pusher tool 1138 can be a blunt tool to fold the cap 1126 down. The divot 1136 in the cap 1126 is located where the cap 1126 attaches to the spinal implant 1100 to allow for bending at the divot 1136. In some embodiments, the cap 1126 forms a hinge with at least one of the side surfaces 1106, 1108.

FIGS. 16A-16D are schematic views of an embodiment of a spinal implant 1200. The spinal implant 1200 can include any of the features of the spinal implant 100 or any of the spinal implants described herein. The spinal implant 1200 can include an upper surface 1202, a lower surface 1204, two side surfaces 1206, 1208, a front surface 1210, a back surface 1212, an opening 1214, features 1216, 1218, a solid body 1220, and a cap 1226. The spinal implant 1200 can include a partially enclosed opening 1214. The opening 1214 is only partially enclosed by the side surfaces 1206, 1208. The cap 1226 can be openable to allow for insertion of the bone graft into the opening 1214. The cap 1226 can be coupled to the two side surfaces 1206, 1208. The cap 1226 can form the back surface 1212 of the spinal implant 1200.

The cap 1226 has a pair of malleable wings 1240 that project from the two side surfaces 1206, 1208 of the open pocket or opening 1214. In some embodiments, an insertion tool (not shown) is configured to cover the wings 1240 protectively as the spinal implant 1200 is inserted in the disc space. When the tool is removed, the wings 1240 act as extensions of the open pocket or opening 1214 to allow for maximal packing bone graft from the position of the spinal implant 1200 all the way to the edge of the disc. If the wings 1240 are too long, they can be cut to proper size. Each side surface 1206, 1208 can include a wing 1240. The wings 1240 can function to extend the side surfaces 1206, 1208 to the cortical rim. The wings 1240 can be incrementally perforated to allow for easy cutting of the excess wings. The wings 1240 can be cut to any length.

In some embodiments, the wings 1240 can be folded back to lock the graft in the opening 1214. The folded wings 1240 can form the back surface of the spinal implant 1200. The folded wings 1240 can enclose or partially enclose the bone graft. The wings 1240 act as a door. Once the pocket or opening 1214 is fully packed, any portion of the wings 1240 that extend beyond the disc entry point can be bent over to close the door and lock the graft in the pocket or opening 1214. The wings 1240 can be scored to facilitate bending them at the appropriate point. In some embodiments, the wings 1240 can be malleable and/or compressible. In some embodiments, the wings 1240 can be rigid. In some embodiments, the wings 1240 can be formed of a polymer material such as PEEK.

Figure 17:
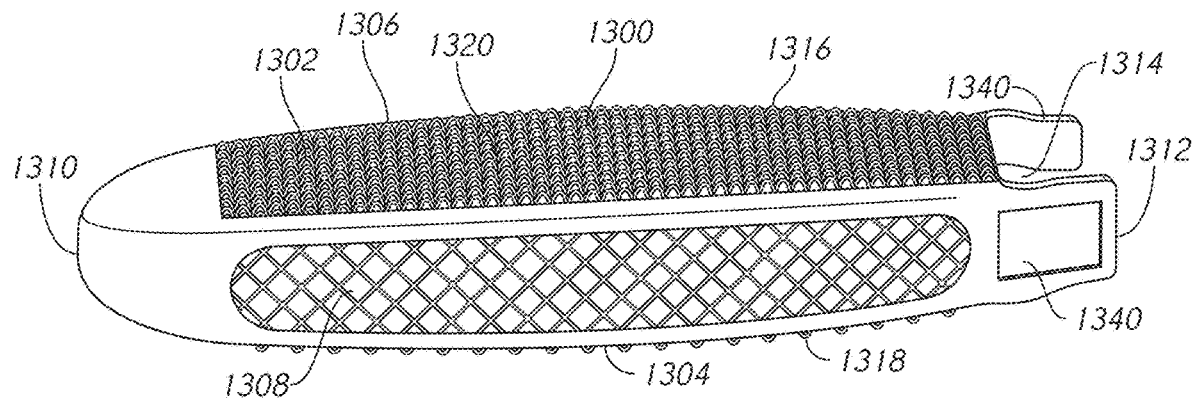
FIG. 17 is a schematic view of an embodiment of a spinal implant.

FIG. 17 is a view of an embodiment of a spinal implant 1300. The spinal implant 1300 can include any of the features of the spinal implant 100 or any of the spinal implants described herein. The spinal implant 1300 can include an upper surface 1302, a lower surface 1304, two side surfaces 1306, 1308, a front surface 1310, a back surface 1312, an opening 1314, one or more features 1316, 1318, and a solid body 1320. The spinal implant 1300 can include a partially enclosed opening 1314. The opening 1314 is only partially enclosed by the side surfaces 1306, 1308. In some embodiments, the back surface 1312 is fully removed. The spinal implant 1300 can include an open back design. In some embodiments, the spinal implant 1300 can include wings 1340 as described herein. The wings of the pocket can be malleable and compressible. The wings 1340 of the pocket can be rigid.

Figure 18:
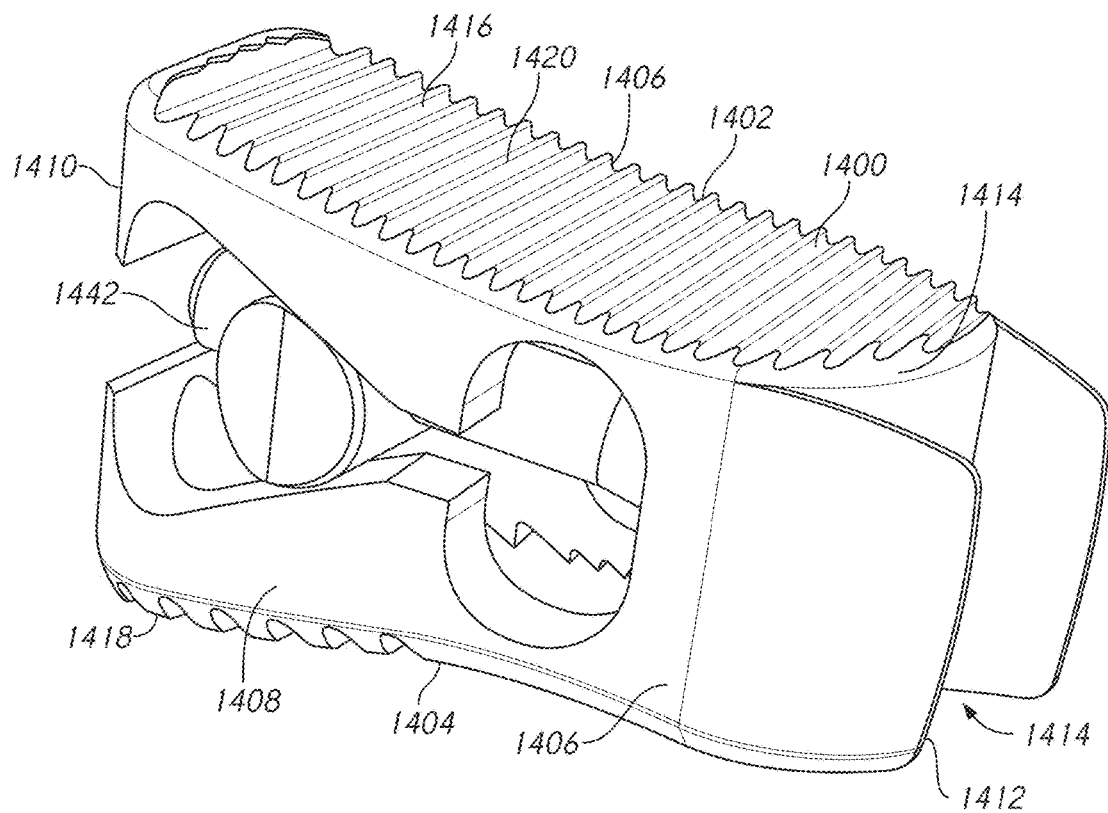
FIG. 18 is a schematic view of an embodiment of a spinal implant.

FIG. 18 is a view of an embodiment of a spinal implant 1400. The spinal implant 1400 can include any of the features of the spinal implant 100 or any of the spinal implants described herein. The spinal implant 1400 can include an upper surface 1402, a lower surface 1404, two side surfaces 1406, 1408, a front surface 1410, a back surface 1412, an opening 1414, one or more features 1416, 1418, and a solid body 1420. The spinal implant 1400 can include a partially enclosed opening 1414. The opening 1414 is only partially enclosed by the side surfaces 1406, 1408. In some embodiments, the back surface 1412 is fully removed. The spinal implant 1400 can be expandable. The spinal implant 1400 can expand in at least one direction. In some embodiments, the spinal implant 1400 can expand in height. In some embodiments, the spinal implant 1400 can expand in width. In some embodiments, the spinal implant 1400 can expand in length. In some embodiments, the spinal implant 1400 can expand such that the upper surface 1402 and the lower surface 1404 are offset. In some methods of use, the spinal implant 1400 is expanded before or after packing bone graft in the pocket or opening 1414. The spinal implant 1400 can be expanded by use of an actuator 1442. In some embodiments, the actuator 1442 is accessible via the pocket or opening 1414. The actuator 1442 can change the distance between two or more surfaces of the spinal implant 1400.

In some embodiments, there is no room for the bone graft in the body of an expandable spinal implant. Designs for an expandable implant can be constrained by requirement to have a central hole. Expandable cages exert tremendous force on endplates. The spinal implant 1400 can solve problems associated with expandable cages. The spinal implant 1400 can provide a large solid surface area. This surface area can correspond with the solid body 1420. The spinal implant 1400 can allow for little to no disc preparation. The spinal implant 1400 can allow decreased operation room time. The spinal implant 1400 can allow no endplate weakening.

The spinal implant can include an improved graft location near one edge of the spinal implant 1400. During insertion, the opening 1414 can be located near the cortical rim of the vertebrae to promote fusion. The spinal implant 1400 can provide an improved graft location near an end of the spinal implant 1400. The spinal implant 1400 can provide compressible and/or radiolucent walls at the graft site, e.g., material selection of the area surround the opening 1414.

Figure 19:
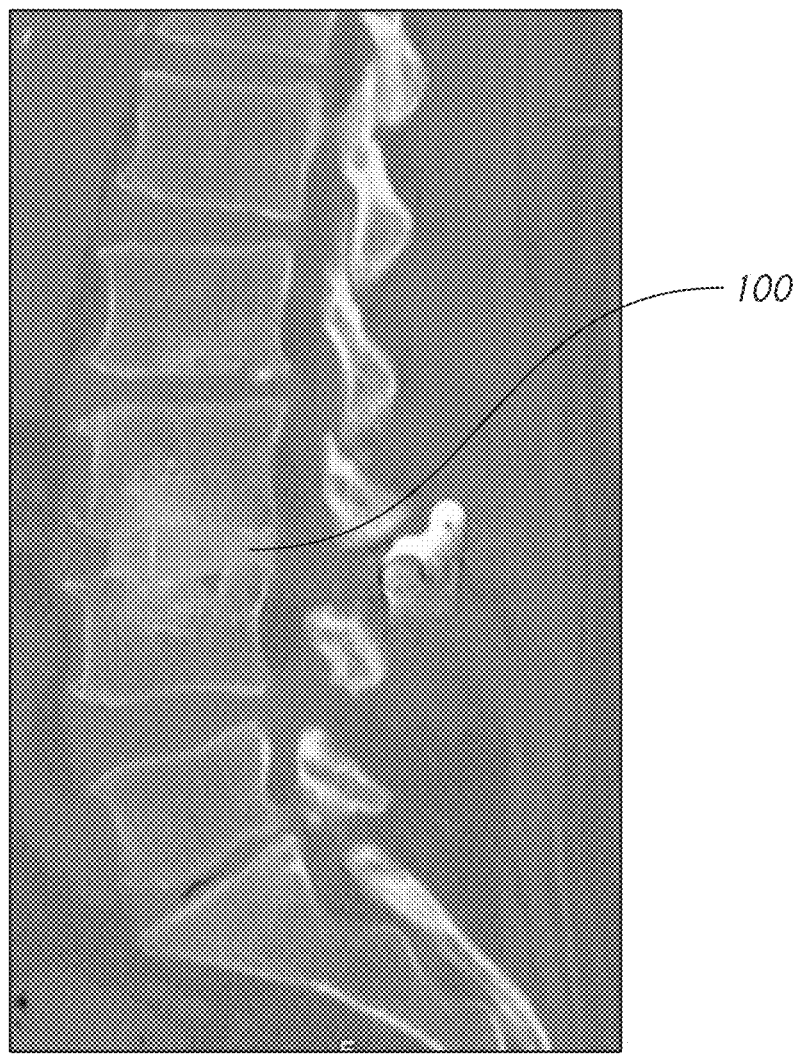
FIG. 19 is a lateral x-ray view of a vertebral column with a schematic illustration of an implant.

FIG. 19 is a lateral x-ray view of a vertebral column. The spinal implant 100 is schematically positioned between lumbar vertebra L3 and lumbar vertebra L4 to illustrate the placement of the spinal implant 100. The spinal implant 100 can extend posterior to the periphery of the disc space. The spinal implant 100 can have a greater height in the center of the disc and a narrower height in the posterior direction. The spinal implant 100 can conform to the normal anatomy of the disc space. In some methods of use, fusion will occur in the posterior area where the L3 and L4 bones are closest to each other.

There are several advantages associated with the implant design and method of use. In some embodiments, an advantage is that there can be a shorter distance for fusion to span. In some methods of use, it can be advantageous to fuse the bones where they are closest together, which occurs at the periphery of the disc. In some embodiments, an advantage is that there is no need for graft extenders. In some embodiments, an advantage is that there is no weakening of central endplates. In some embodiments, an advantage is that there is no need to decorticate bone other than at the entrance to the disc space, right at the periphery of the disc where it's easy to reach and where fusion is intended to occur. In some embodiments, an advantage is that there is increased cage footprint on endplates. In some embodiments, an advantage is that there is no hole in the center of the cage so more surface area contacts the vertebral endplates, therefore less stress risers. In some embodiments, an advantage is to reduce operating room time. In some embodiments, an advantage is to reduce the number of preparation steps, such as the steps to prepare the disc space. In some embodiments, an advantage is that there is no need for extensive disc space cleaning. In some embodiments, an advantage is to just remove enough disc material to make room for the spinal implant 100. In some embodiments, an advantage is that there is no endplate prepping.

Figure 20A:
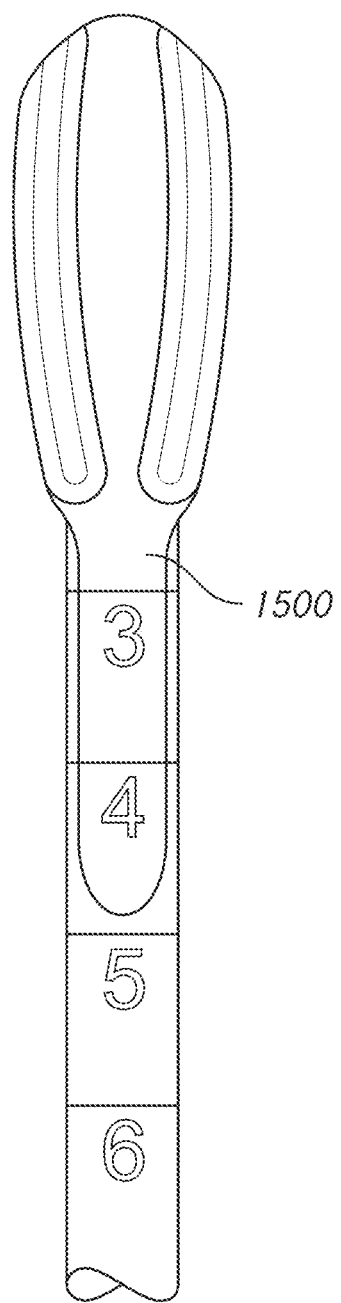
FIGS. 20A-20C are views of a tool 1500 for endplate preparation.
Figure 20B:
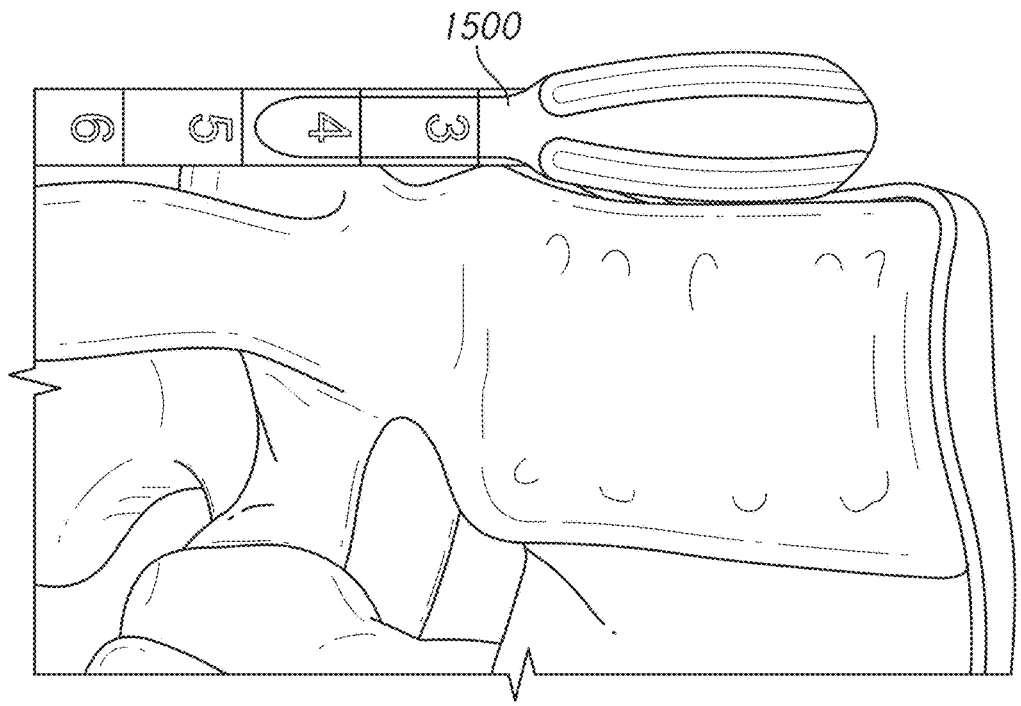
Figure 20C:
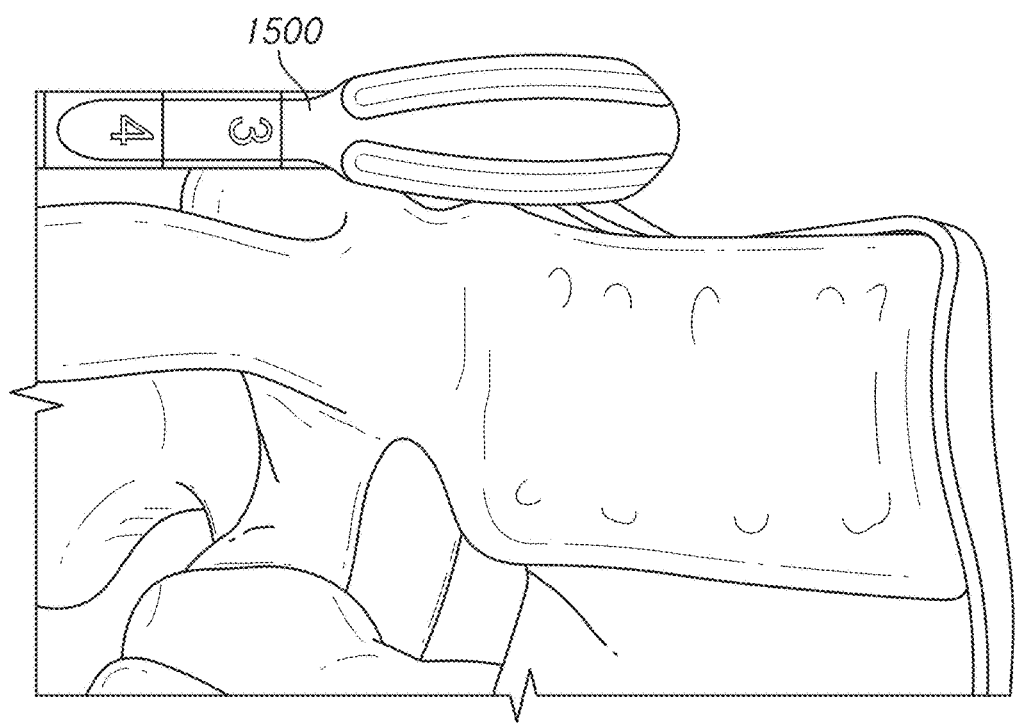
Figure 21:
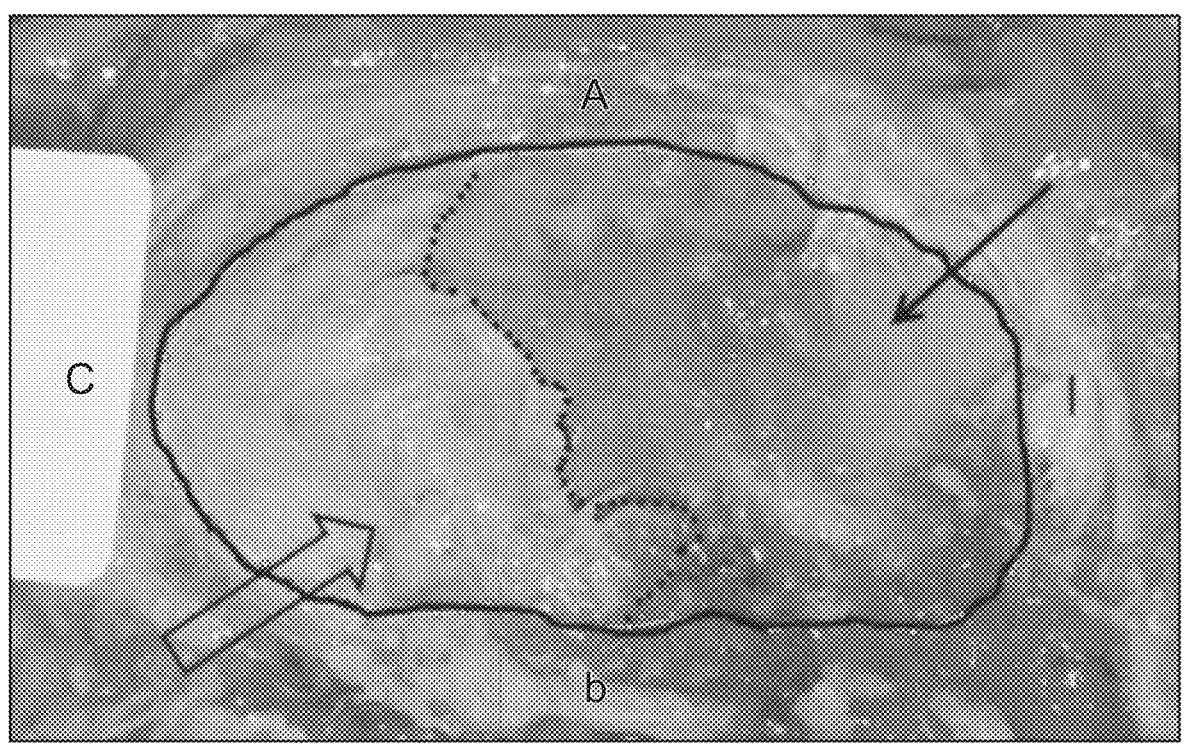
FIG. 21 illustrates an example of the remaining disc material for the posterior ipsilateral approach.

FIGS. 20A-20C is an embodiment of a tool 1500 for endplate preparation. The tool 1500 can facilitate removing disc material to make room for the spinal implant 100. The tool 1500 can facilitate providing an entry location into the disc space. In some methods of use, the tool 1500 may not be useful for removing the disc material from the intervertebral disc space. In recent research, the tool 1500 may not be adequate to prepare the disc space, including incomplete removable of the disc. A study conducted by J. A. Rihn, M.D., et al. and published online in 2014, evaluates the results of disc space preparation for fusion by experienced surgeons. For the anterior contralateral approach, 71.3% of the disc was removed by surface area. For the anterior ipsilateral approach, 72.6% of the disc was removed by surface area. For the posterior contralateral approach, 59.7% of the disc was removed by surface area. For the posterior ipsilateral approach, 83.3% of the disc was removed by surface area. FIG. 21 illustrates an example of the remaining disc material for the posterior ipsilateral approach. The remaining disc material can prevent fusion if the bone graft is positioned adjacent to the vertebral endplates. In some methods of use, the tool 1500 is useful for providing access to the disc space near the cortical rim. In some methods of use, the tool 1500 is useful to decorticate bone near the cortical rim. In some methods of use, the tool 1500 is useful to create bleeding bone near the cortical rim. In some methods of use, the tool 1500 is useful to promote fusion by preparing the cortical rim to engage the bone graft disposed within the opening of the spinal implants described herein.

Figure 22A:
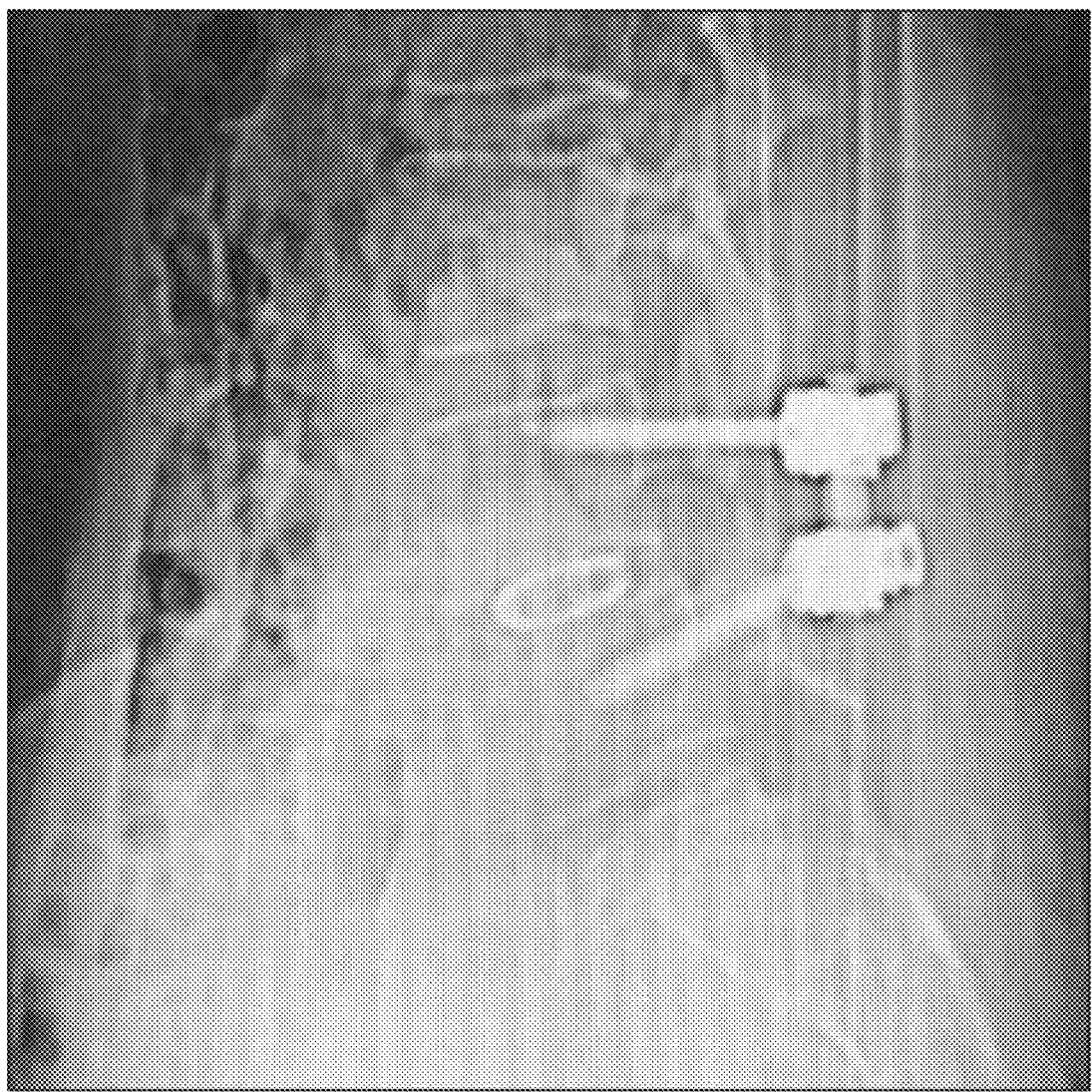
FIGS. 22A-22C are x-ray views of spinal fusion.
Figure 22B:
Figure 22C:

FIG. 22A illustrates an x-ray image and FIGS. 22B-C illustrates CT images of spinal fusion performed with bone graft placed both posterior to and within the cage. Each figure illustrates a spinal implant six months post-operative. Based on methods described herein, there is robust fusion posterior to the spinal implant seen in FIG. 22B whereas there is unsuccessful fusion noted within the cage seen in FIG. 22C. FIGS. 22A-22C represent an example of graft positioning and show commercially available implants. In some embodiments, the solid body 120 of the spinal implant 100 provides structural stability and ligamentotaxis. In some embodiments, the fusion occurs at the periphery of the disc space, where the vertebral bones are strong and the endplates are easy to decorticate. In some embodiments, the graft is at least partially retained by the spinal implant 100 to reduce or prevent graft dislodgement. In some embodiments, the graft is retained in an enclosed opening. In some embodiments, the graft is retained in a partially enclosed opening. In some embodiments, there is a cap to retain the bone graft and prevent posterior migration of the bone graft.

There are several differentiating features of the spinal implants described herein. The opening or pocket for the graft can be offset from the center of the implant. The position of the opening or pocket can allow the bone graft to be in contact with the areas of the vertebral bodies which are easy for the surgeon to decorticate during surgery. This reduces surgical time because there is less disc prep required before the surgeon implants the cage.

The side area of the disc space (the periphery) is an area where the two vertebral bones are the closest to each other. The center of the disc area is where the vertebral bones are the farthest from each other. The spinal implant 100 positions the graft at the point where the two vertebral bones are the closest, and therefore there is less distance for the graft to heal. This more optimal position of the graft and can allow for faster healing (fusion) and higher rate of successful fusion (less incidence of non-union).

In some embodiments, the spinal implant can be designed such that it does not have a hole in the center. The spinal implant 100 can be solid in the center, e.g., solid body 120. This provides greater surface area of the cage against the vertebral endplates above and below, and therefore less chance that the cage will subside into the endplates over time during the during the healing phase (0-6 months post-op). This is an improvement over current spinal implants with their holes in the center. In addition, it may be easier or cheaper to manufacture a solid body instead of a spinal implant with a hole in the center.

In some embodiments, the spinal implant is expandable. There may be additional options for expandable spinal implants design opportunities since the graft is offset from the center. The expandable spinal implant can include actuation and other mechanical features in the center instead of saving room for the graft material opening. There can be a variety of improved designs for expandable and non-expandable spinal implants.

In some methods of use, the surgeon does not have to decorticate the vertebral endplates in their concave central portions. The concave bone area retains the full strength and integrity. This is another reason there may be less subsidence of the spinal implant 100. There can be an increased surface area pushing against non-decorticated endplates which can allow increased spinal manipulation from within the disc space.

In some embodiments, the spinal implant can be designed so that the center portion is more rigid than the periphery, including the area that surround the opening or pocket, such as the wings or cap as described herein. This design can allow stability at the center and compression forces at the periphery. The bone graft can be at the periphery, in the pocket or opening. Bone heals faster and more reliably when under compression (Wolff's Law). The spinal implant with different stiffness in different anatomic areas can enhance the performance of the spinal implant by increasing fusion rate and decreasing time required for healing. The pocket or opening can be made of a more radiolucent material than the body of the cage to allow for visualization of fusion within the pocket region on post operation x-rays.

FIGS. 23A-23F illustrate example method steps which may be utilized in combination with the spinal implant devices described herein. The method steps are merely illustrative. In some embodiments, the spinal implant can be provided to the surgeon in many lengths, widths, and heights. In some methods of use, surgeon selects an appropriate sized spinal implant to fit a particular patient undergoing surgery. Accordingly, all the embodiments of the spinal implant construction disclosed herein can be made in different sizes to accommodate various patients and levels of the spine.

Figure 23B:
FIGS. 23A-23F illustrate methods of use.
Figure 23A:
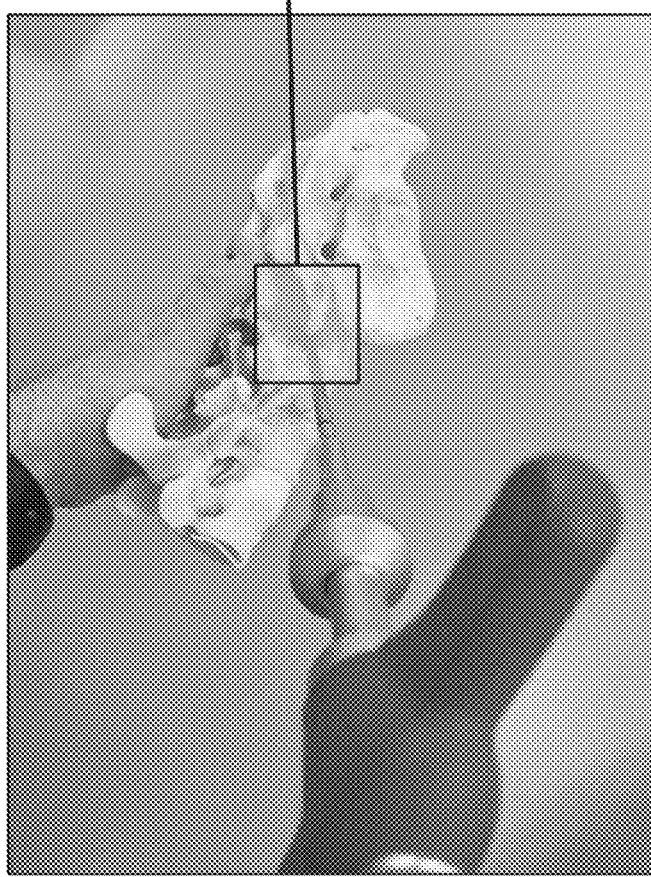
Figure 23C:
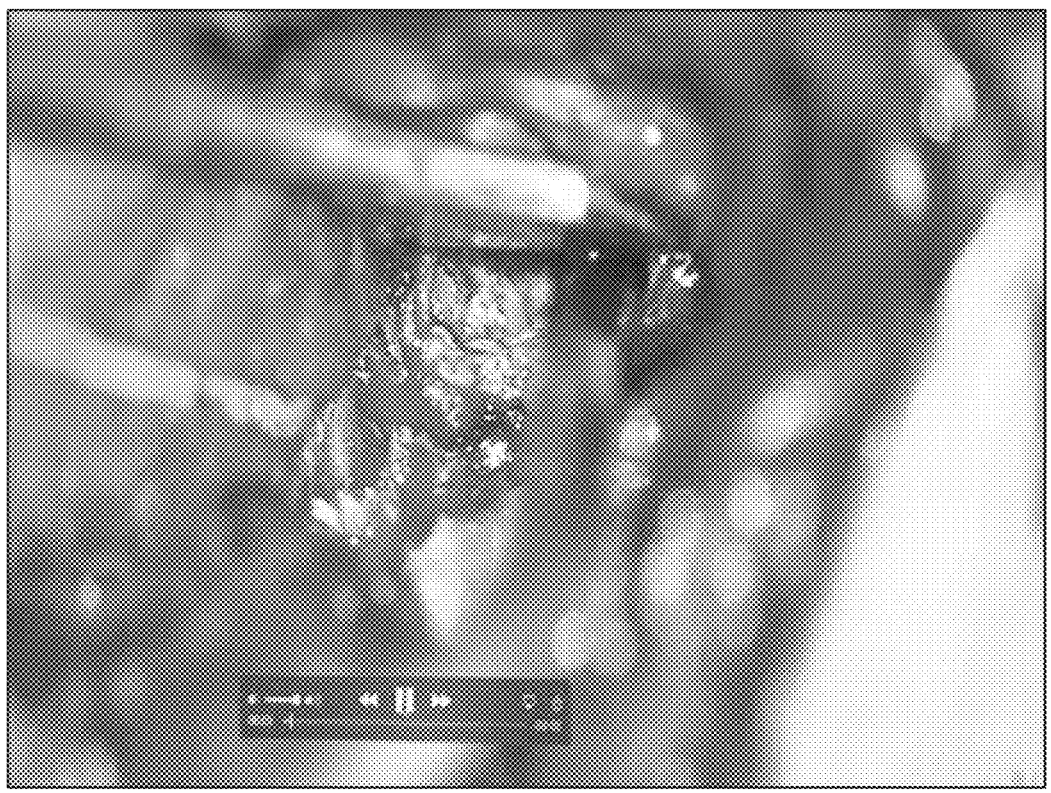
Figure 23D:

FIGS. 23A-23C illustrate use of the tool 1500 illustrated in FIG. 20A. The tool 1500 can be inserted in a flat orientation, parallel to the endplates. The tool 1500 can be rotated to scrape the endplates. In some methods, the curvature of the endplates can make decortication of the endplates difficult. The tool 1500 leaves poor endplate preparation near the center of the endplate, for instance leaving residual cartilage on the endplates. FIG. 23C illustrates rotating the tool 1500. The tissues are distracted to view the tool 1500 which is inserted between the endplates. The endplates are scraped by tool 1500, but it is difficult to view the finished surface area near the center of the endplate. FIG. 23D illustrates removing disc material. The disc material can be after the use of the tool 1500.

In contrast to FIGS. 23A-23D, in some methods, the tool 1500 can be rotated to scrap the cortical rim. The tool 1500 can be particularly well suited to decorticate the cortical rim. The cortical rim is easy to decorticate and complete decortication of the rim can lead to better fusion. In contrast to FIGS. 23A-23D, in some methods, the vertical endplates are not prepared, or not fully prepared. In contrast to FIGS. 23A-23D, in some methods, the disc material is not removed, or not fully removed. This reduces surgical time because there is less disc prep required before the surgeon positions the spinal implant 100. Because a surgeon using the spinal implant 100 does not have to decorticate the concave central portions of the vertebral endplates, those portions of the bones can retain their full strength and integrity. This is another reason that any subsidence of the spinal implant 100 will be unlikely.

Figure 23E:
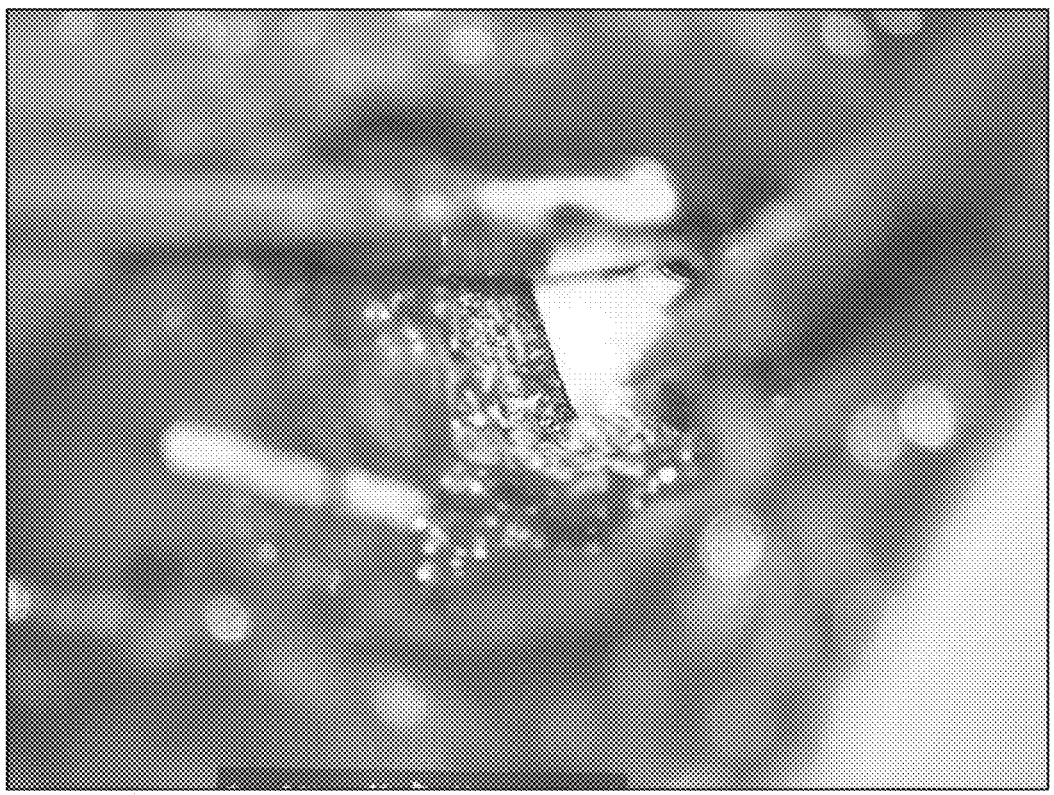
Figure 23F:

FIGS. 23E-23F illustrates an example of a position of a commercial spinal implant. Referring back to FIG. 5, this is an axial or bird's eye view of a vertebral bone. There is a cortical rim on the outside edge of the bone. The cortical rim is an elevated portion of the bone, whereas the cancellous region is a concave portion of the bone. A typical cage is seated in the concave portion and a hole for depositing graft material is located at the center of the cage body so that the graft comes into contact only with the concave region of the vertebral bone. In some methods, there can be post-packing of bone graft. Additional graft material can be packed into the disc space, posterior to the implant. In some methods, the additional graft material is not retained by the commercial spinal implant.

In contrast with these method steps, the spinal implant 100 is designed to position the graft material near the cortical rim, and at least partially enclose the graft material. The far lateral end regions of the disc space (the periphery) are where the two vertebral bones are closest to one another. The center of the disc space is where the vertebral bones are the farthest apart. Depositing graft in an opening or open pocket 114 in a far lateral end portion of the spinal implant 100 places the graft at a point where the two vertebral bones are closest, so there is less distance over which the graft needs to heal and fuse. This more optimal placement of the graft should allow for faster healing (fusion) and a higher rate of successful fusions (less incidence of non-union).

The method utilizing spinal implant 100 can include placing the opening 114 at the periphery of the disc space. The method can include positioning the spinal implant 100, wherein the end opposite the opening 114 is configured to be inserted first into the vertebral space. The method utilizing spinal implant 100 can include inserting the implant in an anterior direction. The method utilizing spinal implant 100 can include inserting the implant in a posterior direction. The method utilizing spinal implant 100 can include inserting the implant in a lateral direction.

In some methods of use utilizing spinal implant 100, part of the spinal implant 100 is positioned in the concave region of the vertebral bones; however, the pocket or opening 114 is positioned at an end portion of the spinal implant 100, so that the graft comes into contact with the cortical rim on the each of the bones. Unlike commercial spinal implants, the spinal implant 100 does not require that a hole for receiving bone graft material be formed in a center region of the spinal implant 100. This provides a further advantage in that more surface area of the spinal implant 100 can come into contact with the vertebral endplates, thus preventing the spinal implant 100 from subsiding into the vertebral bone above or below over time. As a result, the spinal implant 100 can provide more stability. In some embodiments, the spinal implant 100 has a better chance of promoting a successful fusion.

In some methods of use, the spinal implant 100 at least partially contains the graft material. In some methods of use utilizing spinal implant 100, the bone graft is inserted into the opening 114 or pocket before insertion of the spinal implant 100. In some methods of use utilizing spinal implant 100, the bone graft is inserted into the opening 114 or pocket after insertion of the spinal implant 100. The method can include positioning the spinal implant 100, wherein at least a portion of an edge of the opening 114 collapses at least one millimeter (e.g., one mm, two mm, three mm, four mm, five mm, six mm, seven mm, eight mm, nine mm, ten mm, or any range of the valves). The method can include placing bone graft in contact with the cortical rim. The method can include positioning the spinal implant 100 such that the rim applies a compressive force to the bone graft.

In some embodiments, the pocket or opening 114 for receiving bone graft material is relatively long and extends along one end portion of the spinal implant 100. The opposite far lateral end portion of the spinal implant 100 can be closed as shown in FIG. 4A, open as shown in FIG. 8, or made with a closure mechanism such as a cap as disclosed herein. The pocket or opening 114 for depositing graft can be in contact with the cortical rim area of the vertebral bone. In some embodiments, the center of the spinal implant 100 is solid, so more surface area of the body is in contact with the weaker cancellous bone. Thus, the vertebral endplates can concentrate their compression forces against the central portion of the spinal implant.

The material that forms the pocket or opening 114 does not need to be the same as that of the rest of the spinal implant 100. In some embodiments, the sides of the pocket or opening 114 can be softer and more malleable (such as silastic or thin metal) so that the sides can collapse a few millimeters as the spinal implant settles in place after surgery during a several month's long healing phase. Such collapse would allow a compressive force to be exerted on the bone graft which is desirable since, under Wolff's Law, bone tends to heal better under compression and does not heal well when shielded from stress. The lateral end portion of the spinal implant 100 that extends to the periphery of the disc need not necessarily have a structurally supportive function, instead, these portions can collapse or compress thereby compressing the bone graft. In contrast, commercial spinal implant designs with hole for depositing bone graft in the center of the spinal implant can prevent compressive forces from being fully applied on the deposited graft. That is, the body immediately surrounding the hole tends to shield the graft from the compressive forces if the opening is in the center of the implant.

In some embodiment, the spinal implant 100 or a portion thereof is made to mimic the modulus of elasticity of normal bone. The solid body of the spinal implant 100 can possess the quality of mimicking healthy bone. In some embodiments, the far end portions of the spinal implant 100 are preferably more elastic, flexible, compressible, or collapsible than the modulus of elasticity of normal bone so that graft deposited in those regions is not stress-shielded but is subjected to at least slight compression. The far end portions of the spinal implant 100 can be more elastic, flexible, compressible, or collapsible based on material selection or design considerations such as thickness. The spinal implant 100 can be constructed so that the central portion of its body is more rigid than the end portions, such as portions near the opening. This will allow stability at the center of the body, and for compression forces to act at the periphery of the body where the bone graft is present. In some methods, the patient can heal faster and more reliably if the bone graft is maintained under compression. By having less stiffness at the end portions of the body than at the central region of the body, the spinal implant can increase the fusion rate and decrease the time required for healing.

Figure 24A:
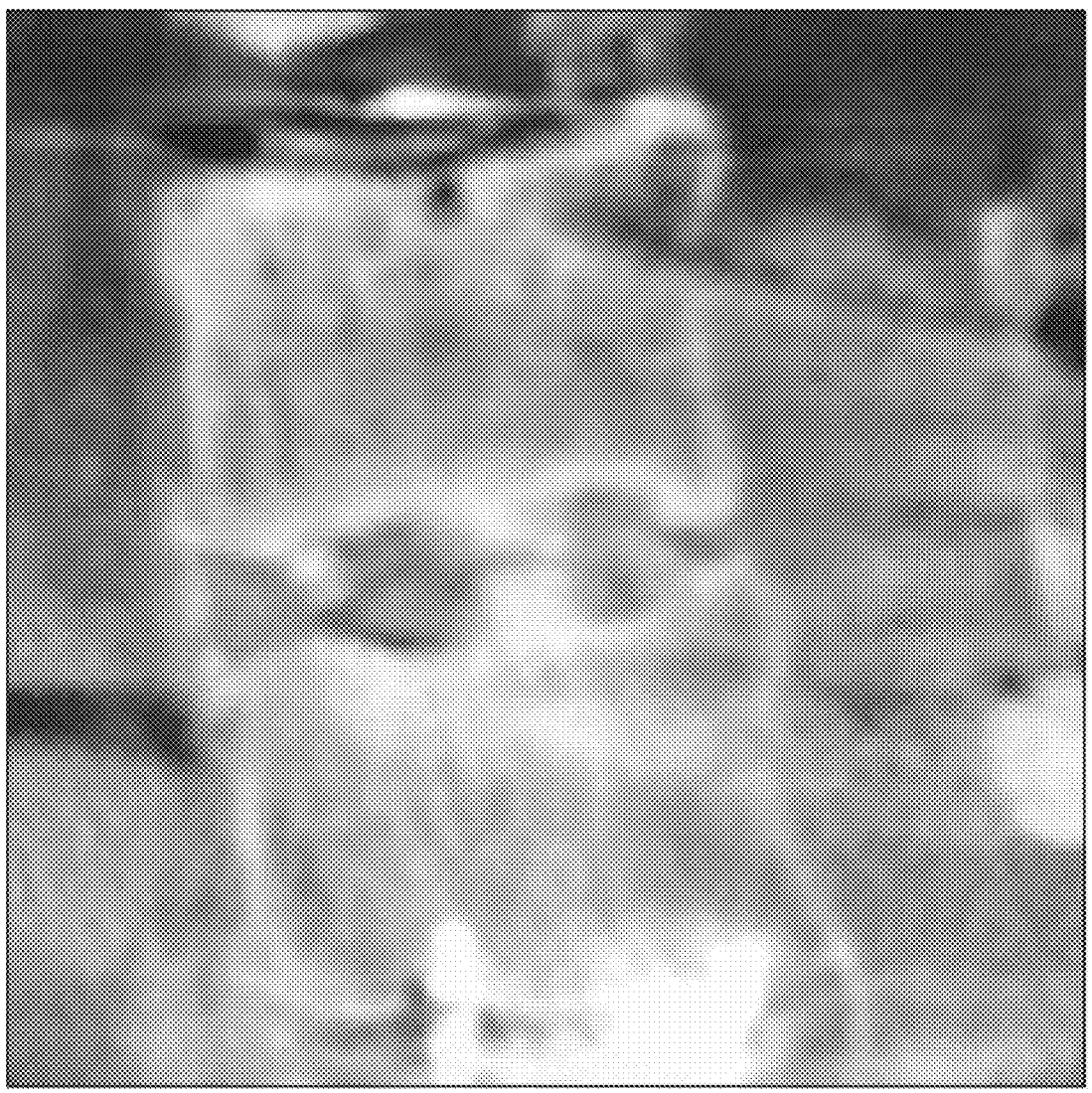
FIGS. 24A and 24B are x-ray views of typical post-operative outcomes.
Figure 24B:

The method of use can be in contrast to methods of use including an implant with a central hole. In other methods of use, the spinal implant does not extend to the peripheral area. The only area available for bone grafting is in the center of the spinal implant where the spinal implant is widest. The center spot is where the bones are farthest apart. In this method of use, it is more difficult for fusion to develop in this center spot than if the graft is located at a far lateral or peripheral area. The spinal implant does not require a hole to be formed in the central region of its body. In some embodiments, the spinal implant can be solid in the central region so as to interpose more surface area of the body against the vertebral endplates above and below, with less chance that the cage will subside into the endplates over time during the healing phase (0-6 months post-op). FIGS. 24A and 24B are x-ray views of typical post-operative outcomes showing subsidence and non-union.

Referring back to FIG. 18, the spinal implant extends posterior to the periphery of the disc space. The area available for bone grafting is at a far lateral end portion of the spinal implant where the spinal implant is most narrow. It is easier for fusion to develop in this far lateral spot than at the center since, as mentioned, this is where the bones are closest to one another.

Although the present invention has been described in relation to various exemplary embodiments, various additional embodiments and alterations to the described embodiments are contemplated within the scope of the invention. Thus, no part of the foregoing description should be interpreted to limit the scope of the invention as set forth in the following claims. For all of the embodiments described above, the steps of the methods need not be performed sequentially.

What is claimed is:

1. A spinal implant comprising:
    an upper surface, wherein at least a portion of the upper surface is configured to contact an endplate of an upper vertebral body;
    a lower surface, wherein at least a portion of the lower surface is configured to contact an endplate of a lower vertebral body;
    a front end and a back end, wherein the front end is configured for insertion into a space between the upper vertebral body and the lower vertebral body;
    a first side extending between the upper surface and the lower surface;
    a second side extending between the upper surface and the lower surface;
    a first flange projecting from the first side;
    a second flange projecting from the second side; and
    a pocket located at the back end, wherein the pocket is partially enclosed by the first flange and the second flange, wherein the pocket is configured to contain graft material that spans between a cortical rim of the upper vertebral body and a cortical rim of the lower vertebral body.

2. The spinal implant of claim 1, wherein the first flange and the second flange are compressible.

3. The spinal implant of claim 1, wherein the first flange and the second flange comprise a polymer material.

4. The spinal implant of claim 1, wherein a center portion of the spinal implant is more rigid than a portion near the pocket.

5. The spinal implant of claim 1, wherein the spinal implant comprises different stiffness in different areas.

6. The spinal implant of claim 1, wherein the pocket comprises a radiolucent material.

7. The spinal implant of claim 1, wherein the cortical rim of the upper vertebral body and the cortical rim of the lower vertebral body are configured to apply a compressive force to the graft material in the pocket.

8. The spinal implant of claim 1, wherein a portion of the spinal implant is configured to mimic a modulus of elasticity of bone.

9. The spinal implant of claim 1, wherein a central region of the spinal implant is solid.

10. The spinal implant of claim 1, wherein the front end comprises an opening.

11. The spinal implant of claim 1, further comprising:
    a third flange projecting from the first side;
    a fourth flange projecting from the second side;
    a second pocket located at the front end, wherein the second pocket is partially enclosed by the third flange and the fourth flange, wherein the second pocket is configured to contain graft material.

12. The spinal implant of claim 11, wherein the spinal implant comprises a bullet shape to conform to a curvature of the endplate of the upper vertebral body and the endplate of the lower vertebral body.

13. The spinal implant of claim 11, wherein the upper surface, the lower surface, or both the upper surface and the lower surface comprise projections.

14. The spinal implant of claim 11, wherein the spinal implant is formed by 3D printing.

15. A method of spinal fusion comprising:
    providing a spinal implant comprising:
        an upper surface, a lower surface, a front end, a back end, a first side, a second side, a first flange projecting from the first side, a second flange projecting from the second side, and a pocket located at the back end;
    inserting the spinal implant into a space between an upper vertebral body and a lower vertebral body, wherein at least a portion of the upper surface contacts an endplate of the upper vertebral body and at least a portion of the lower surface contacts an endplate of the lower vertebral body; and packing the pocket with graft material, wherein the graft material spans between a cortical rim of the upper vertebral body and a cortical rim of the lower vertebral body.

16. The method of claim 15, wherein the first flange and the second flange are compressible.

17. The method of claim 15, wherein the cortical rim of the upper vertebral body and the cortical rim of the lower vertebral body apply a compressive force to the graft material in the pocket.

18. The method of claim 15, wherein the cortical rim of the upper vertebral body and the cortical rim of the lower vertebral body are decorticated.

19. The method of claim 15, wherein packing the pocket with the graft material comprising packing the pocket with the graft material after inserting the spinal implant into the space between the upper vertebral body and the lower vertebral body.

20. The method of claim 15, wherein packing the pocket with the graft material comprising packing the pocket with the graft material before inserting the spinal implant into the space between the upper vertebral body and the lower vertebral body.

* * * * *